United States Patent
Bondhus et al.

(10) Patent No.: US 9,919,145 B2
(45) Date of Patent: *Mar. 20, 2018

(54) CONNECTOR ASSEMBLIES FOR RECEIVING IMPLANTABLE MEDICAL LEADS

(71) Applicant: MEDTRONIC, INC., Minneapolis, MN (US)

(72) Inventors: Spencer M. Bondhus, Columbia Heights, MN (US); Patrick D. Wells, North Oaks, MN (US)

(73) Assignee: MEDTRONIC, INC., Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/070,808

(22) Filed: Mar. 15, 2016

(65) Prior Publication Data
US 2016/0193458 A1    Jul. 7, 2016

Related U.S. Application Data

(63) Continuation of application No. 14/212,091, filed on Mar. 14, 2014, now Pat. No. 9,283,372.
(Continued)

(51) Int. Cl.
*A61N 1/00* (2006.01)
*A61N 1/05* (2006.01)
(Continued)

(52) U.S. Cl.
CPC ............ *A61N 1/05* (2013.01); *A61N 1/0558* (2013.01); *H01R 24/58* (2013.01); *H01R 25/003* (2013.01)

(58) Field of Classification Search
CPC .... A61N 1/0472; A61N 1/048; A61N 1/0488; A61N 1/05; A61N 1/0558; A61N 1/0595; H01R 2201/12; H01R 13/17–13/187
See application file for complete search history.

(56) References Cited

U.S. PATENT DOCUMENTS

| | | |
|---|---|---|
| 4,328,813 A | 5/1982 | Ray |
| 4,995,389 A | 2/1991 | Harris |

(Continued)

FOREIGN PATENT DOCUMENTS

| | | |
|---|---|---|
| CN | 202236888 U | 5/2012 |
| DE | 4232627 A1 | 4/1993 |

OTHER PUBLICATIONS

DBS/Advance, DBS Extensions with eXtend Technology, St. Jude Medical, 2011.
(Continued)

*Primary Examiner* — Scott Getzow
(74) *Attorney, Agent, or Firm* — Withers & Keys, LLC

(57) ABSTRACT

Connector assemblies that are separate from medical lead extensions provide features such as bores for receiving both a medical lead and a medical lead extension and provide electrical connections between connectors of the leads and connectors of the lead extensions. Connector assemblies may include additional features such as contours and wings that reduce subcutaneous erosion. Connector assemblies may also include retention structures such as movable clips that are moved into engagement with leads and lead extensions to retain them within the connector assembly. Integrated lead extension connectors may also include contours and wings as well as retention structures including movable clips.

2 Claims, 32 Drawing Sheets

Related U.S. Application Data

(60) Provisional application No. 61/781,608, filed on Mar. 14, 2013.

(51) Int. Cl.
*H01R 24/58* (2011.01)
*H01R 25/00* (2006.01)

(56) References Cited

U.S. PATENT DOCUMENTS

| | | |
|---|---|---|
| 5,354,326 A | 10/1994 | Comben et al. |
| 5,489,225 A | 2/1996 | Julian |
| 5,545,188 A | 8/1996 | Bradshaw et al. |
| 5,951,595 A | 9/1999 | Moberg et al. |
| 6,044,304 A | 3/2000 | Baudino |
| 6,134,477 A | 10/2000 | Knuteson |
| 6,210,417 B1 | 4/2001 | Baudino et al. |
| 6,356,792 B1 | 3/2002 | Errico et al. |
| 6,428,368 B1 | 8/2002 | Hawkins et al. |
| 6,430,442 B1 | 8/2002 | Peters et al. |
| 6,473,654 B1* | 10/2002 | Chinn ............ A61N 1/05 600/375 |
| 7,580,756 B2 | 8/2009 | Schulte et al. |
| 7,981,119 B2 | 7/2011 | Lando et al. |
| 7,988,674 B2 | 8/2011 | Adams et al. |
| 7,993,352 B2 | 8/2011 | Black et al. |
| 8,182,540 B2 | 5/2012 | Lin et al. |
| 8,355,786 B2 | 1/2013 | Malinowski |
| 8,355,787 B2 | 1/2013 | Barker |
| 8,556,860 B2 | 10/2013 | Stratton et al. |
| 8,738,151 B2 | 5/2014 | Nelson |
| 2002/0143376 A1* | 10/2002 | Chinn ............ A61N 1/05 607/115 |
| 2004/0230268 A1* | 11/2004 | Huff ............ A61N 1/05 607/116 |
| 2007/0250077 A1 | 10/2007 | Skakoon et al. |
| 2009/0264943 A1* | 10/2009 | Barker ............ A61N 1/05 607/2 |
| 2010/0029127 A1 | 2/2010 | Sjostedt |
| 2011/0022100 A1 | 1/2011 | Brase et al. |
| 2012/0035616 A1* | 2/2012 | Olsen ............ A61N 1/05 606/129 |
| 2012/0083867 A1 | 4/2012 | Wahlstrand et al. |
| 2012/0157924 A1 | 6/2012 | Schutz et al. |
| 2012/0259386 A1 | 10/2012 | DeRohan et al. |
| 2013/0204336 A1* | 8/2013 | Sharma ............ A61N 1/0558 607/117 |

OTHER PUBLICATIONS

U.S. Appl. No. 14/212,091, filed Jun. 29, 2015 Non-Final Rejection.
U.S. Appl. No. 14/212,091, filed Sep. 29, 2015 Amendment/Reconsideration.
U.S. Appl. No. 14/212,091, filed Oct. 29, 2015 Notice of Allowance.
U.S. Appl. No. 14/212,091, filed Jan. 29, 2016 Amendment After Notice of Allowance (Rule 312).
U.S. Appl. No. 14/212,091, filed Feb. 16, 2016 Response to Amendment Under Rule 312.
PCT/US2015/060394 International Search Report and Written Opinion dated Feb. 22, 2016.
U.S. Appl. No. 14/212,091, filed Feb. 24, 2016 Issue Notification.
U.S. Appl. No. 14/939,613, filed Mar. 15, 2017 Non-Final Rejection.
U.S. Appl. No. 14/939,613, filed Jun. 15, 2017 Amendment/Reconsideration.
U.S. Appl. No. 14/939,613, filed Jul. 21, 2017 Notice of Allowance.

* cited by examiner

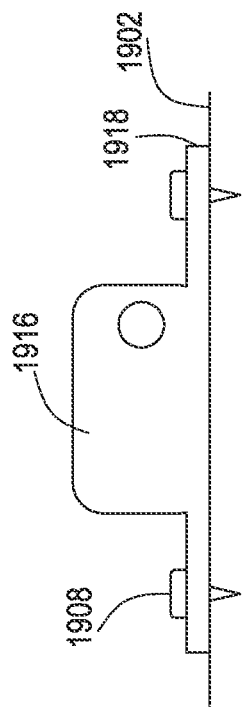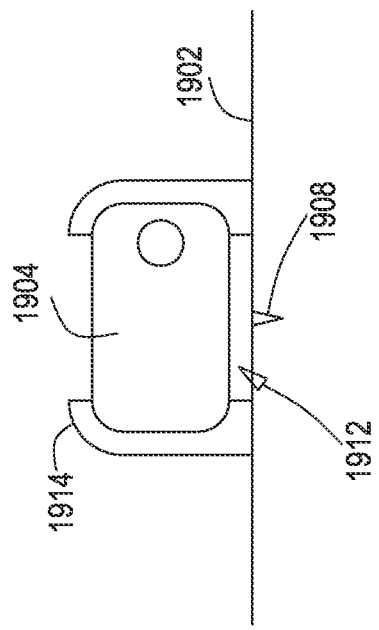

CONNECTOR ASSEMBLIES FOR RECEIVING IMPLANTABLE MEDICAL LEADS

TECHNICAL FIELD

Embodiments are related to implantable medical devices. More particularly, embodiments relate to connector assemblies that receive implantable medical leads requiring a lead extension.

BACKGROUND

Electrical stimulation may be used as a form of therapy for several medical conditions. A stimulation device is implanted into the body at a particular location that is convenient for implantation, and the stimulation device provides electrical stimulation signals. A conduction path is created for the electrical stimulation signals by the presence of an implantable medical lead that includes individual conductive filars that are connected to electrodes on a distal end. The electrodes are positioned at a target site within the body to deliver the stimulation signals.

The implantable medical leads are often made at a length that is less than the distance from the target site to the implantation site of the stimulation device. This may be done to allow the implantable medical leads to be more easily tunneled into position at the target site than would be the case if the lead was significantly longer. This allows for a two-stage implantation where a lead extension is also used, which provides protection for the implanted lead and allows the implanted lead to remain in place if the extension needs to be replaced. The lead extension is positioned between the stimulation device and the implantable lead, and a distal end of the lead extension is an extension connector that receives a proximal end of the implantable lead. The proximal end of the lead includes electrical contacts that establish electrical connection with connectors within the extension connector, while filars extend between the proximal contacts of the extension and the electrical connectors within the extension connector located on the distal end of the extension. Thus, conduction paths from the stimulation device to the electrodes of the implantable lead are achieved.

There are drawbacks to this configuration that utilizes an extension. The extension connector may constrain the tunneling to a single direction. Furthermore, the extension connector on the distal end of the extension requires a different manufacturing method than proximal end of the extension which increases the costs and complexities of manufacturing of the extension. Additionally, the geometry of the extension connector may lead to discomfort for the patient and/or erosion of tissue beneath the skin of the patient.

SUMMARY

Embodiments address issues such as these and others by providing various alternatives to the conventional extension connector. One such alternative includes a connector assembly that is separate from the extension and that receives a distal end of the extension and a proximal end of the lead. In this manner, the distal end of the extension may be manufactured in the same manner as the proximal end and may also be small enough to be tunneled in either direction including to the location of the proximal end of the implantable lead from the pocket of the stimulator. Furthermore, the connector assembly may be constructed in a relatively compact manner, may include compact retention structures to hold the lead and extension in place, and/or may include structures with contours that lessen the likelihood of erosion of tissue beneath the skin. Another such alternative is an extension with an extension connector that includes compact retention assemblies and/or includes structures with contours that lessen the likelihood of erosion.

Embodiments includes a connector assembly for receiving an implantable medical lead and a lead extension that includes a body housing a first bore with an external opening and a second bore with an external opening. The body includes a plurality of insulative spacers having apertures that are aligned adjacently to define the first bore and the second bore. A first plurality of electrical connectors further define the first bore, each electrical connector of the first plurality of electrical connectors being separated from an adjacent electrical connector of the first plurality electrical connectors by an insulative spacer of the plurality of insulative spacers. A second plurality of electrical connectors that further define the second bore, the electrical connectors of the first plurality being paired and electrically coupled to corresponding electrical connectors of the second bore.

Embodiments provide a connector assembly for receiving an implantable medical lead and a lead extension that includes a body housing a first bore with an external opening and a second bore with an external opening. The second bore is adjacent to the first bore, with the first bore and the second bore defining substantially parallel longitudinal axes. An electrically conductive member is located within the body and extends laterally relative to the longitudinal axes, with the electrically conductive member defining a first electrical connector aligned in the first bore and a second electrical connector aligned in the second bore.

Embodiments provide a connector assembly for receiving an implantable medical lead and a lead extension that includes a body housing a first opening and a second opening and defining a first bore. A first electrical connector is present at the first bore within the body and aligned with the first opening and completely encircles the circumference of the first bore. A second electrical connector is disposed within the body. An electrical conductor is located within the body that electrically couples the first electrical connector to the second electrical connector.

Embodiments provide an implantable lead extension for receiving an implantable medical lead that includes an elongated insulative body having a proximal end and a distal end. A plurality of electrical connectors is located on the proximal end, and a plurality of filars is present within the elongated body and is electrically connected to corresponding electrical connectors. An extension connector assembly is permanently attached to the distal end of the elongated body. The extension connector assembly includes a body having a first bore and a groove perpendicular to the first bore, the groove housing a movable clip. The movable clip has a springable end such that movement of the clip moves the springable end into and out of alignment with the first bore. A plurality of electrical connectors is located within the first bore, and the plurality of filars is electrically connected to corresponding electrical connectors within the first bore.

Embodiments provide an implantable lead extension for receiving an implantable medical lead that includes an elongated insulative body having a proximal end and a distal end. A plurality of electrical connectors is located on the proximal end, and a plurality of filars is present within the elongated body and is electrically connected to corresponding electrical connectors. An extension connector assembly is permanently attached to the distal end of the elongated body. The extension connector assembly includes a body having a first bore, the body also having a tapered wing that extends outwardly through the plane. A plurality of electrical connectors is located within the first bore, and the plurality of filars is electrically connected to corresponding electrical connectors within the first bore.

Embodiments provide an implantable lead extension for receiving an implantable medical lead. The extension includes an elongated insulative body having a proximal end and a distal end and a plurality of electrical connectors on the proximal end. A plurality of filars is present within the elongated body and is electrically connected to corresponding electrical connectors. An extension connector assembly is permanently attached to the distal end of the elongated body, and the extension connector assembly includes a body housing a first bore and a spring loaded retention structure within the first bore.

Embodiments provide an implantable lead extension for receiving an implantable medical lead. The extension includes an elongated insulative body having a proximal end and a distal end and a plurality of electrical connectors on the proximal end. A plurality of filars is present within the elongated body and being electrically connected to corresponding electrical connectors. An extension connector assembly is permanently attached to the distal end of the elongated body, and the extension connector assembly includes a body housing a first bore and a twist lock retention structure aligned with the first bore.

DESCRIPTION OF THE DRAWINGS

FIGS. 18A-18D show various examples of a connector assembly being anchored within a patient.

DETAILED DESCRIPTION

Embodiments provide alternatives to conventional lead extension connectors. Some embodiments provide connector assemblies that are separate from the lead extension where both the lead extension and the lead are inserted into the connector assemblies. Some embodiments provide extension connectors or separate connector assemblies that include retention structures to hold the lead and/or extension in a fixed position once inserted into the connector assembly. Some embodiments provide extension connectors or separate connector assemblies with a contoured shape to lessen the erosion and discomfort that otherwise may occur due to abrupt transitions in the shape of a connector, where the contoured shape may provide wings that facilitate anchoring.

Figure 1:
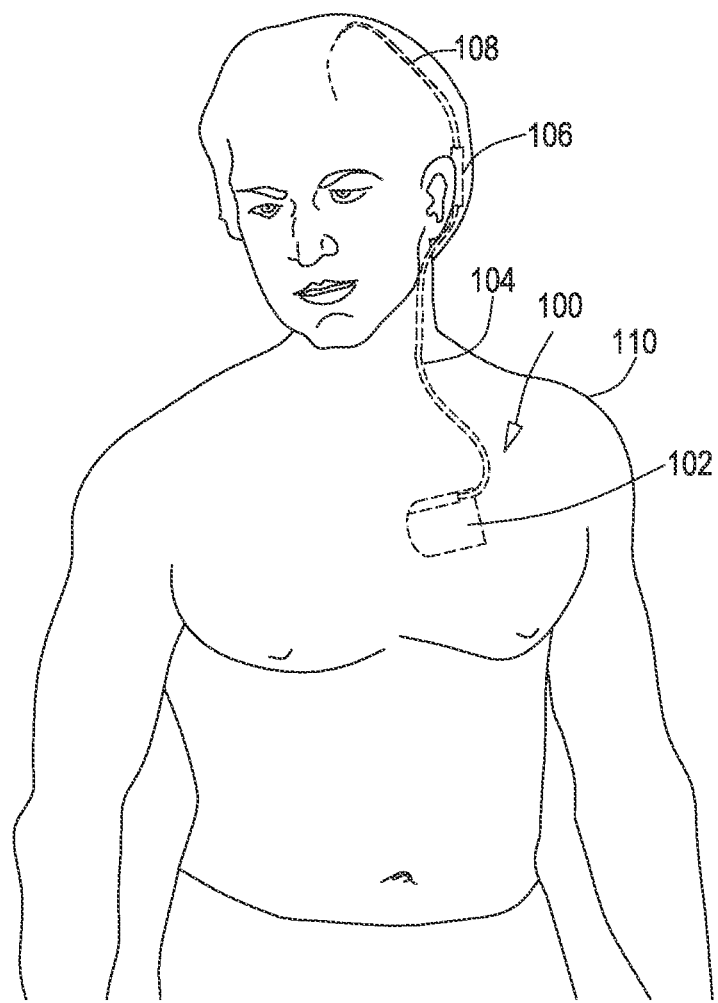
FIG. 1 shows an implantable medical system that includes a connector assembly for receiving an implantable medical lead.

FIG. 1 shows a typical operating environment for the various embodiments. In this example, the embodiments are being used in the context of deep brain stimulation. However, the embodiments may be used in other contexts as well including spinal cord stimulation and peripheral nerve stimulation where a lead extension is used to extend the electrical pathway from a stimulation device to the implantable lead and/or where multiple lead extensions are connected in series to even further lengthen the electrical pathway.

In FIG. 1, an implantable stimulation system 100 includes a stimulation device 102, a lead extension 104, a connector 106, and a lead 108 that are implanted within the body 110 of the patient. The lead extension 104 is coupled to the stimulation device 102 and extends to the location of the proximal end of the lead 108. The connector 106, which may be permanently attached to the extension 104 or may be a separate connector assembly, receives the proximal end of the lead 108. Within the connector 106, each electrical pathway from the extension 104 is bridged to the corresponding electrical pathways of the lead 108.

Figure 2:
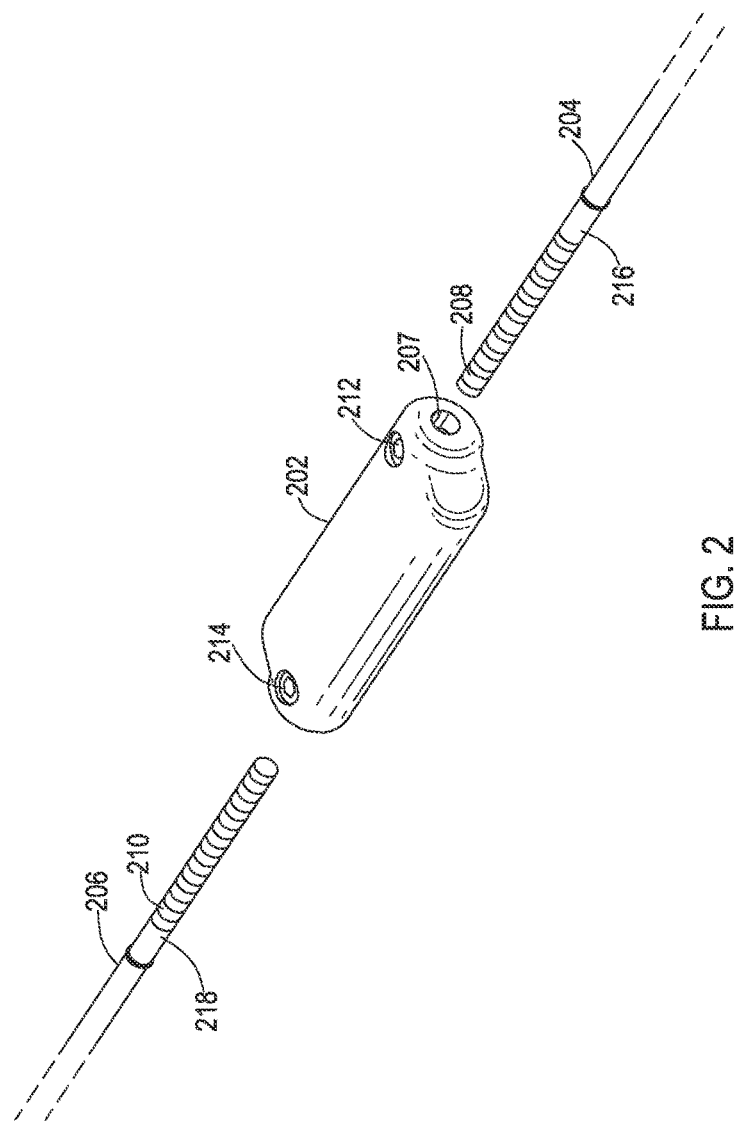
FIG. 2 shows a first example of a connector assembly that receives both an implantable medical lead extension and an implantable medical lead.

FIG. 2 shows an example of a connector assembly 202 that may form the connector 106 of FIG. 1. In FIG. 2, the connector assembly 202 is formed of a body that houses a bore 207 that receives the proximal end of the lead 204. In this example, the connector assembly 202 includes a bore on the opposite side that receives the distal end of the lead extension 206. The connector assembly 202 includes retention features such as set screw assembly 212 which retains the proximal end of the lead 204 via contact of a set screw against a contact 216 and set screw assembly 214 which retains the distal end of the lead extension 206 via contact of a set screw against a contact 218. While this example shows the lead 204 and the lead extension 206 having the same diameter, and therefore both bores of the connector assembly 202 being of the same diameter, it will be appreciated that the bores may be constructed at different diameters so as to accommodate a lead extension of a different diameter than the lead. However, where the bores are the same diameter and the electrical connectors of both bores are at the same pitch, the connector assembly 202 is reversible.

Figure 3:
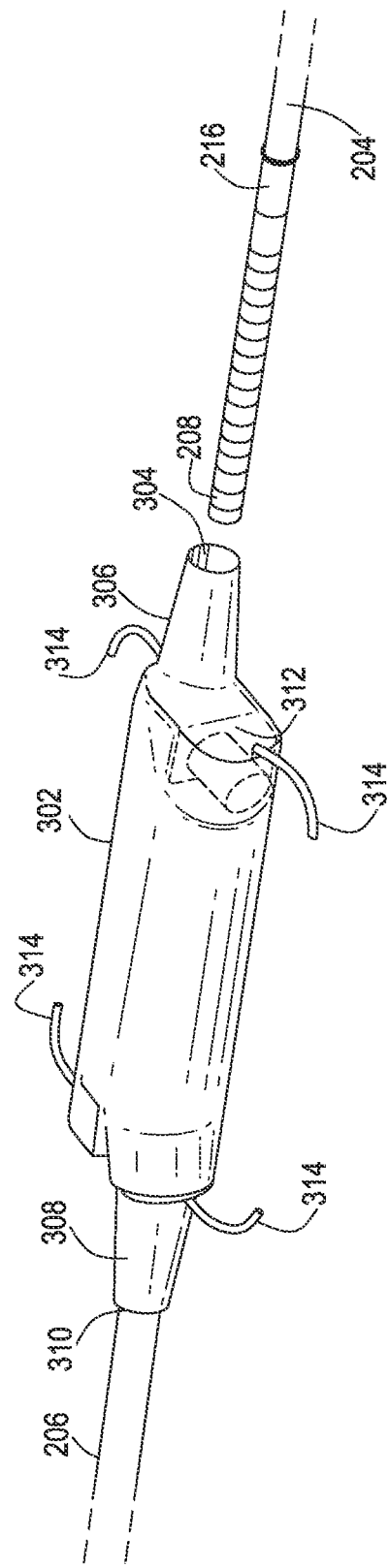
FIG. 3 shows a second example of a connector assembly that includes strain relief.

FIG. 3 shows another example of a connector assembly 302 This embodiment includes a strain relief 306 on the side of the lead 204 and a strain relief 308 on the side of the extension 206. The strain relief 306 includes an opening 304 to the bore of the connector assembly 302 which receives the proximal end of the lead 204. The strain relief 308 also includes an opening 310 to the bore of the connector assembly which receives the distal end of the extension 206. The connector assembly 302 also includes retention features such as the set screw assembly 312 which retains the extension 206 and lead 204. As shown, the set screw assembly retains the lead 204 by contact of a set screw against the clink 216. In this example, the set screw assembly is oriented 90 degrees from the set screw assemblies 212, 214 of FIG. 2.

For embodiments where the distal end of the lead extension and the proximal end of the lead have electrical connectors at the same pitch and at the same diameter, then the corresponding connector assembly is reversible as either bore of the connector assembly can receive either the distal end of the lead extension or the proximal end of the lead. Furthermore, the lead extension may also be reversible where the proximal end and the distal end utilize the same pitch for the electrical connectors and where either end may be placed within the bore of a stimulation device and either end may be placed into the bore of the connector assembly. Where the lead extension utilizes the same pitch on both ends and where the proximal end of the lead utilizes the same pitch as the lead extension, then three out of the four ends involved in the extension-to-lead chain may be manufactured by the same process. Examples of structures for establishing the pitch of the bores in the connector assembly are shown in FIGS. 4, 5, and 16A-16K.

The example of FIG. 3 also includes tines 314. These tines 314 provide retention of the connector assembly position at the implanted location by engaging surrounding tissue. Because the connector assembly is separate from the extension lead, the connector assembly is not required to be tunneled and therefore, the tines 314 do not present problems during the implantation.

Figure 4:
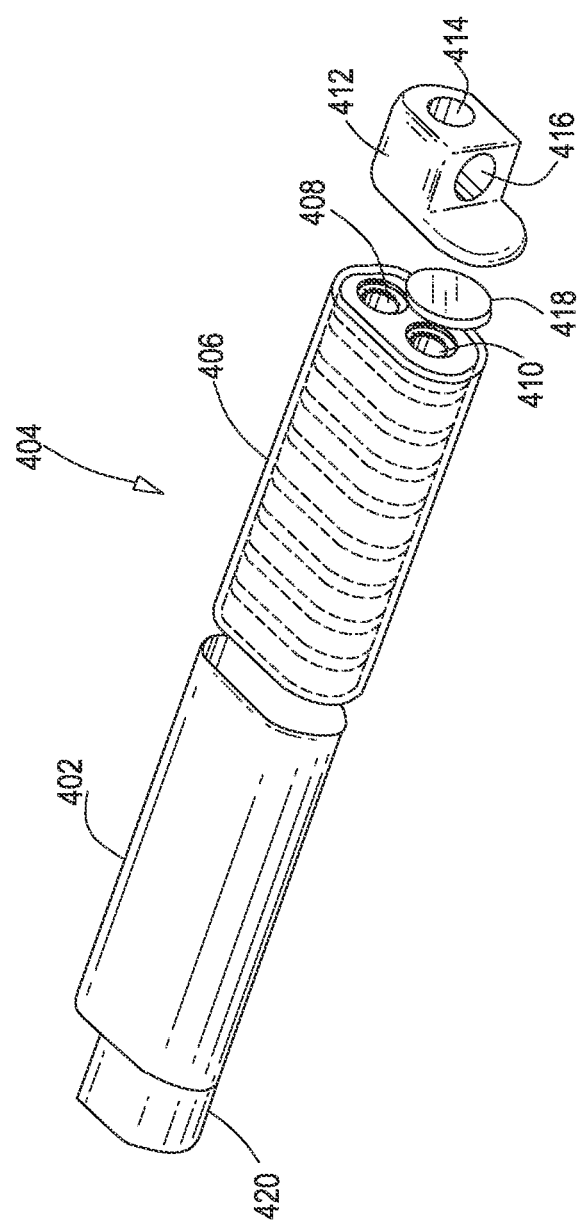
FIG. 4 shows a partially exploded view of an example of the connector assembly.

FIG. 4 shows a partially exploded view of an embodiment of a connector assembly. This connector assembly includes a sub-assembly 404 that includes electrical connectors and intervening insulative spacers that are discussed in more detail below with reference to FIG. 5. An insulative coating 406 may then be overcoated around the electrical connectors and insulative spacers within the sub-assembly 404 to form a body. The sub-assembly 404 defines two adjacent and substantially parallel bores 408, 410 for receiving the lead from one direction and lead extension from the other. Each bore is capped via an insulative cap 418 that may be a separate piece or may be integral and that isolates the bore from the set screw block of the adjacent bore. Each end of the sub-assembly 404 includes a retention structure such as a set screw block 412 and 420. The set screw blocks have a bore 414 to receive the lead or extension that aligns with one of the bores 408, 410, and a bore 416 contains the set screw.

In this example, the sub-assembly 404 is installed within an outer shell 402 which may be constructed of a metal or other rigid material and completes the connector assembly. The set screw blocks 412, 420 may be welded to the edges of the shell 402. This may provide the added feature of creating continuity for a shield that may be present within the lead and lead extension for purposes of avoid induced currents from ambient RF energy such as during a magnetic resonance imaging (MRI) scan. The shield of the lead and the extension may be electrically coupled to the contact that is electrically coupled to the set screw assemblies 412 and 420 which are electrically coupled together by the conductive shell 402. The conductive shell 402 may be exposed to the tissue, which would provide a ground for the shield, or the conductive shell 402 may be covered by an over-molded insulative material which would prevent a grounding of the shield. As other alternatives, the conductive shell 402 may be electrically connected to set screw blocks of each bore that are used to provide a stimulation path or the set screw blocks and the shell 402 may be electrically isolated from all other electrical pathways.

Figure 5:
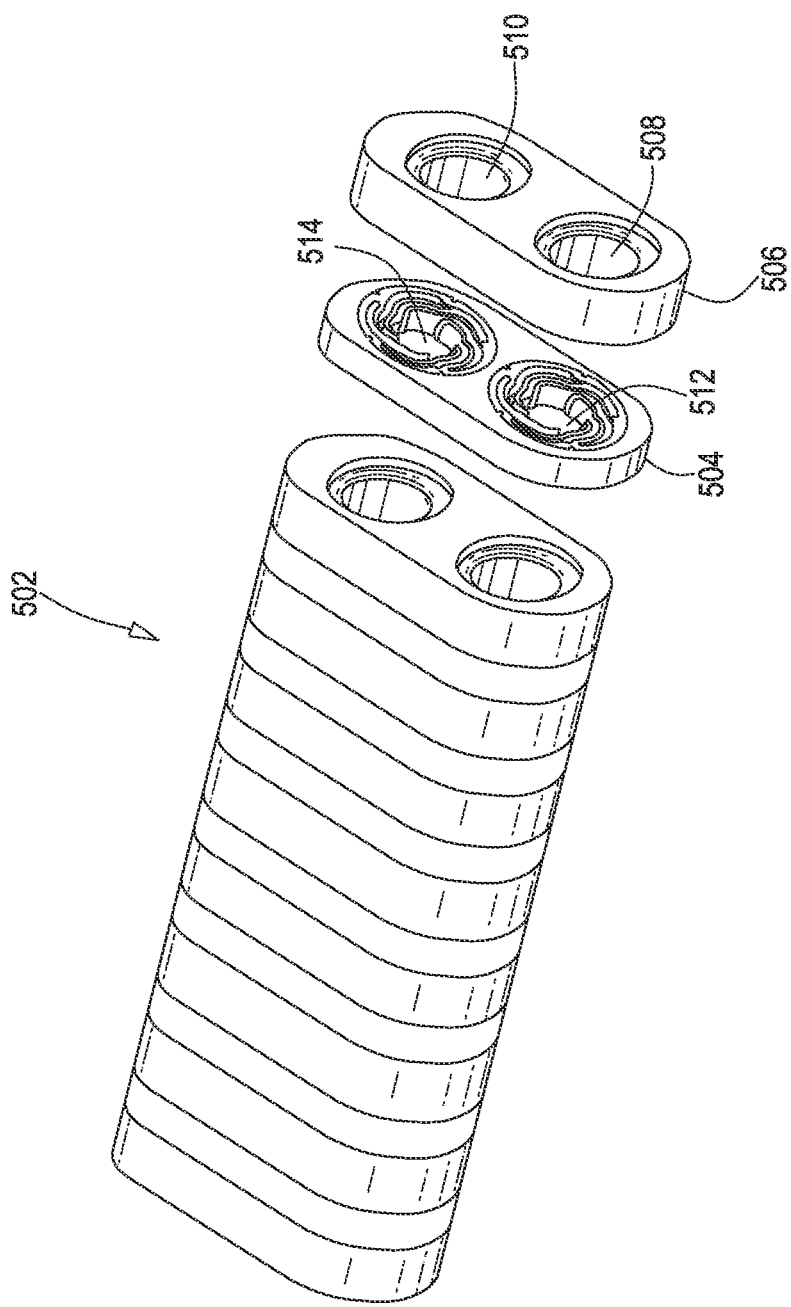
FIG. 5 shows a partially exploded view of stacked configuration of electrical connectors and insulative spacers of a connector assembly.

FIG. 5 shows an example of a sub-assembly 502 of a connector assembly. This sub-assembly 502 includes insulative spacers 506 and electrical connector bodies 504 positioned in an immediately adjacent and interleaved fashion. Both the insulative spacers 506 and electrical connector bodies 504 have apertures 508, 510 and 512, 514, respectively, that together form the bores of the connector assembly that receive the lead and extension. As can be seen apertures 508, 510 are aligned adjacently, as are apertures 512, 514. The resulting bores of this example are adjacent and substantially parallel to each other with the electrically connector bodies 504 extending laterally to the axis of the bores. The insulative spacers 506 form seals at the apertures 508, 510 which prevent fluids from spanning from one electrical connector body 504 to the next and thereby prevent inadvertent electrical connections from occurring.

Each electrical connector body 504 provides the electrical connection from an electrical connector of the extension to an electrical connector of the lead. Because the electrical connector bodies 504 each have two electrical connectors that are coupled by the conductive nature of the electrical body 504 establishing an electrically conductive pathway and are thereby paired together, no intervening electrical conductor is necessary. Thus, no wires are needed within the connector assembly. However, it will be appreciated that in other embodiments, different electrical connectors may be utilized where separate wires are used to electrically couple them together. For instance two canted coil connectors such as the Bal Seal® connectors may be used instead and either encased in a common conductive housing or interconnected by wiring.

While FIG. 5 shows a stacked configuration of the electrical connector bodies 504 and the insulative spacers 506 that are overcoated for stability and cohesiveness, other types of construction may also be used in other embodiments. For instance, a rigid carrier constructed of a plastic or other rigid non-conductive material may be provided to hold each connector body 504 and each insulative spacer 506 in the proper interleaved position.

For some embodiments, the electrical contacts may be present in one bore and be separated by insulative spacers while the other bore is a series of electrical contacts, such as set screw blocks with air gaps rather than seals. Thus, the bore with set screw blocks and air gaps retains compatibility with very low insertion force extensions or leads while the other bore provides seals for extensions or leads where higher insertion forces are acceptable.

Figure 6:
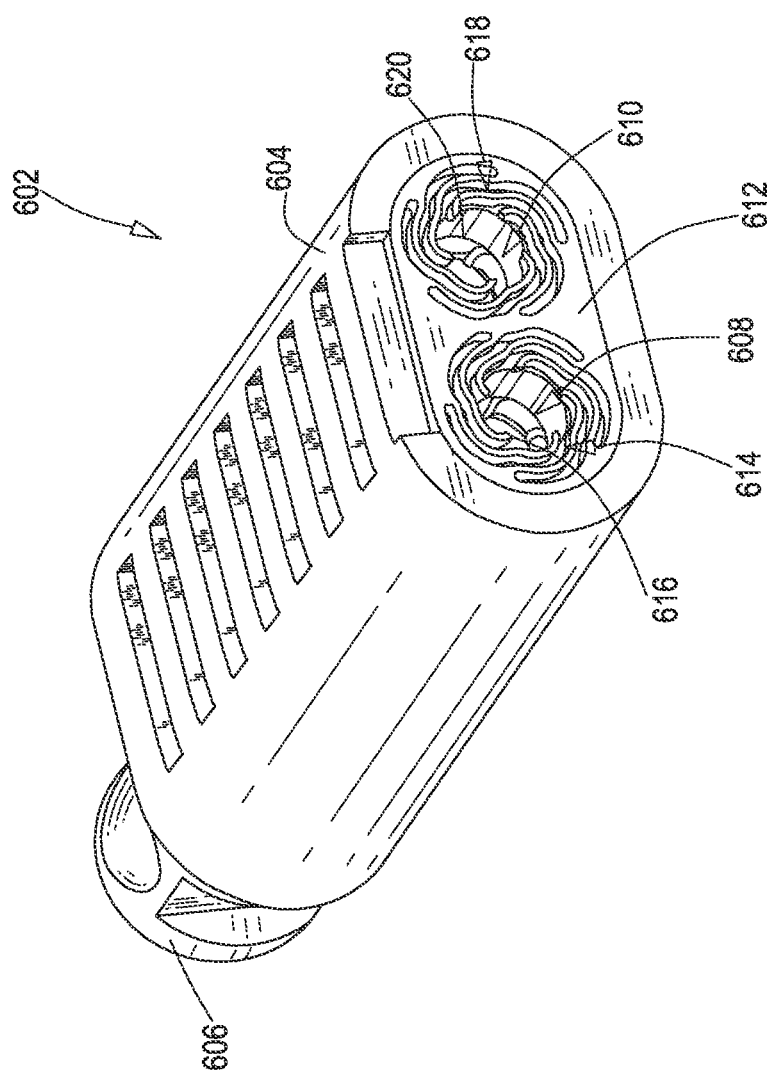
FIG. 6 shows a cross-sectional view of a connector assembly utilizing a single piece dual connector configuration within a carrier.

FIG. 6 provides a cross-sectional view of a sub-assembly 602 of a connector assembly. This sub-assembly 602 includes electrical connector bodies 612 as well as a carrier 604 that provides integral insulative spacers which are not visible in this view, where the electrical connector bodies are inserted through the visible openings of the carrier 604. In this example, the layer 604 may complete the body of the connector assembly, such as where the sub-assembly 602 is not covered by a rigid outer shell as discussed above in FIG. 4. The sub-assembly 602 is attached to a retention structure, such as a set screw assembly 606 that may be attached to the layer 604 by being partially over-molded, glued, and the like. The sub-assembly 602 may also be overcoated.

The electrical connector bodies 612 of this example are constructed of a conductive material such as a biocompatible metal with relatively high elasticity including Ti-15Mo (Titanium Molybdenum alloy) and TNTZ (Tantalum, Niobium, Titanium, Zirconium), and each includes two electrical connectors 614, 618 that define bores 608, 610 for receiving electrical connectors of the lead and lead extension. In this example, the electrical connectors 614, 618 are single piece connectors that are formed by individual leaves 616, 620 distributed about the connector 614, 618. These leaves 616, 620 flex in the radial direction to receive the lead or lead extension while being biased against the electrical connector of the lead or lead extension and establish proper electrical continuity from the connector of the extension to the connector of the lead. In this particular example, these single piece connectors are formed so that they completely encircle the circumference of the bore for receiving the lead or lead extension, with individual leaves 616, 620 partially encircling the circumference.

Figure 7:
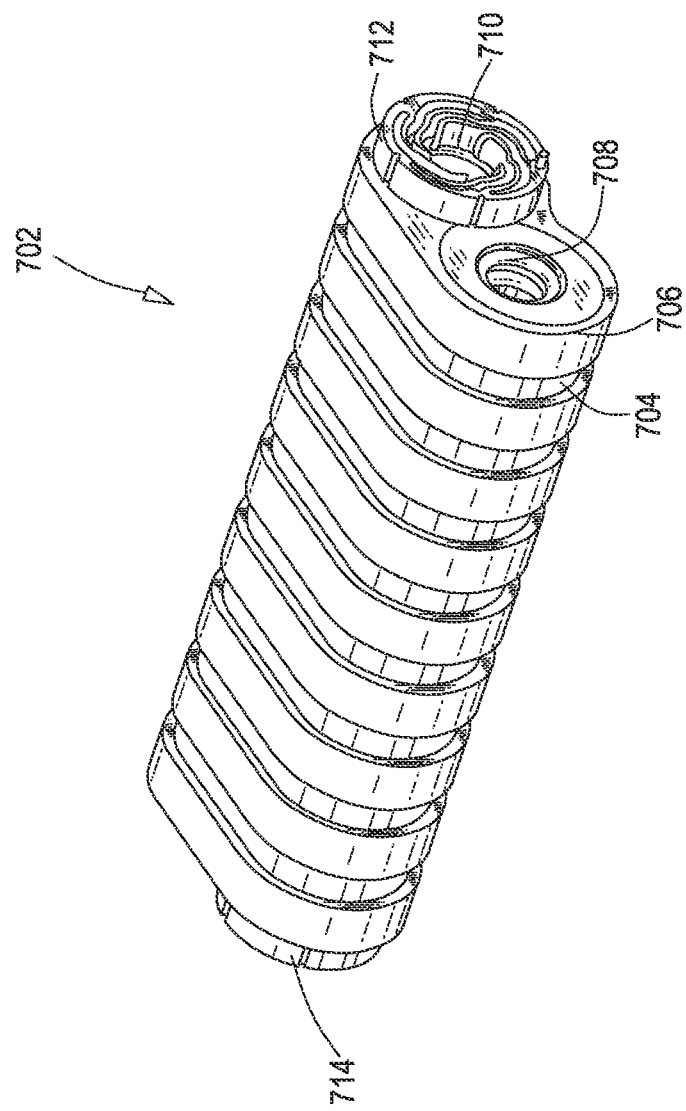
FIG. 7 shows another example of a stacked configuration of electrical connectors and insulative spacers of a connector assembly.

FIG. 7 shows an example of another sub-assembly 702 which also includes interleaved electrical connector bodies 604 and insulative spacers 706, which define bores 708, 710. However, in this example, the sub-assembly 702 includes electrical connector bodies 710, 714 that form only one single piece connector. This construction may be used where set screw assemblies are not present to retain the lead but where shield continuity is desired by electrically connected a clink of the extension to a clink of the lead. In that case, one connector body 710 connects to one clink while the other connector body 714 connects to the other clink. Another conductor then electrically couples the connector bodies 710, 714 together, such as by using an outer conductive layer like the shell 402 of FIG. 4 where the outer conductive layer makes contact with the connector bodies 710, 714 but is insulated from the connector bodies 704.

Figure 8:
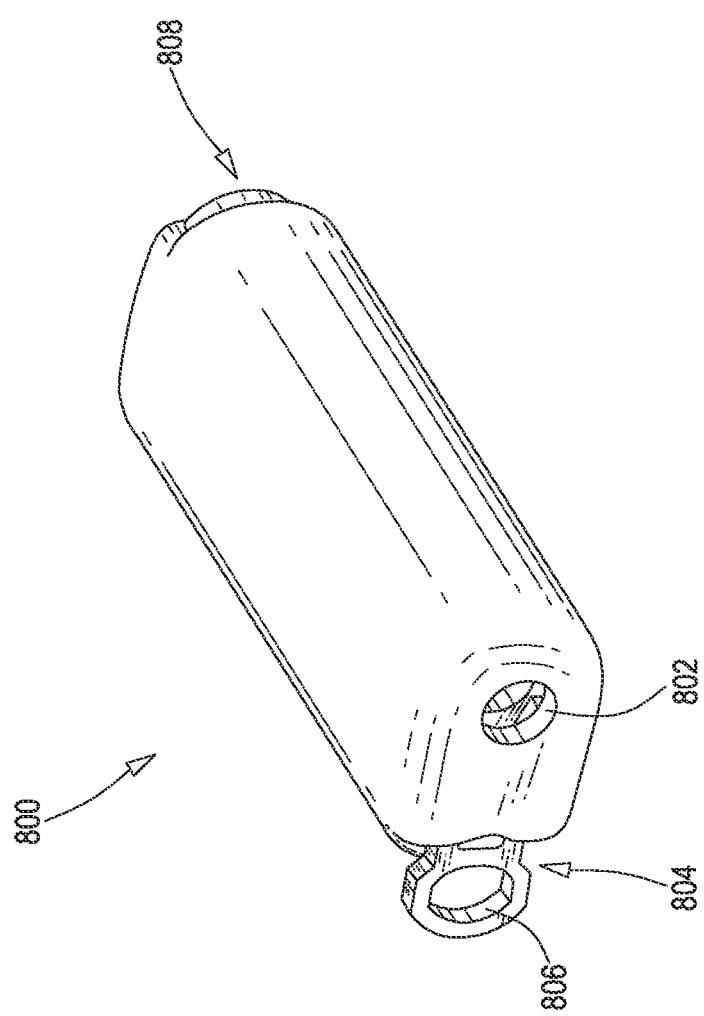
FIG. 8 shows an example of a connector assembly that receives both a lead extension and an implantable medical lead while including a compact retention structure.
Figure 9:
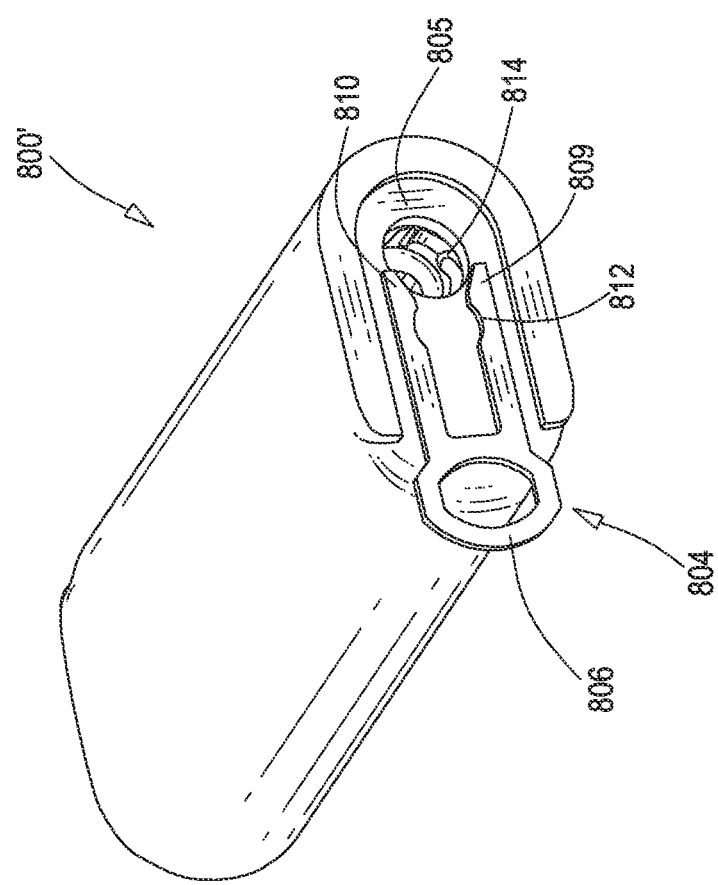
FIG. 9 shows a cross-section of the example of FIG. 8.

In order to eliminate the set screw assemblies for some embodiments, another retention structure is provided. One example of such a retention structure is shown in FIGS. 8 and 9. A connector assembly 800 includes a movable clip 804, 808 on each end. Each clip 804, 808 includes a handle portion 806 which slides within a groove 805 which is shown in the cross-sectioned connector assembly 800' of FIG. 9. This allows the clip 804, 808 to slide relative to the outer opening 802 and corresponding bore 814.

Each movable clip 804, 808 includes prongs 809, 810 that are springable to a more open position. This allows the prongs 809, 810 to be moved onto a lead body or clink as the clip 804, 808 is being pushed inward. The lead body or clink settles into detents 812 in the prongs 809, 810 where the detents 812 align with the bore 814. The handle portion 806 is partially exposed when the clip is engaged on the lead or lead extension so that any available tool that can catch on the exposed portion of the handle 806. The clip 804, 808 can then be pulled outward to release the lead or lead extension from the clip 804, 808.

The movable clip 804, 808 may be constructed of a biocompatible non-conductor such as a plastic. Where the clip 804, 808 can serve as part of a shield ground or where the clip 804, 808 connects only to an insulative portion of the lead or extension, the clip 804, 808 may also be a biocompatible metal.

Other examples of retention structures that eliminate set screw blocks are also possible. For example, the connector assembly may be provided with a twist lock attachment, for instance a Tuohy-Bourst connector. Other examples include spring loaded mechanisms with a trigger. For example, a spring-assist could be attached to the clip 804, 808 with a small catch formed in the groove to hold the clip 804, 808 in the outward position. Upon a slight push by the surgeon inward to overcome the catch, the spring-assist may then force the clip 804, 808 onto the lead or lead extension. Additional examples such as these are discussed below in relation to FIGS. 20-24.

Figure 10:
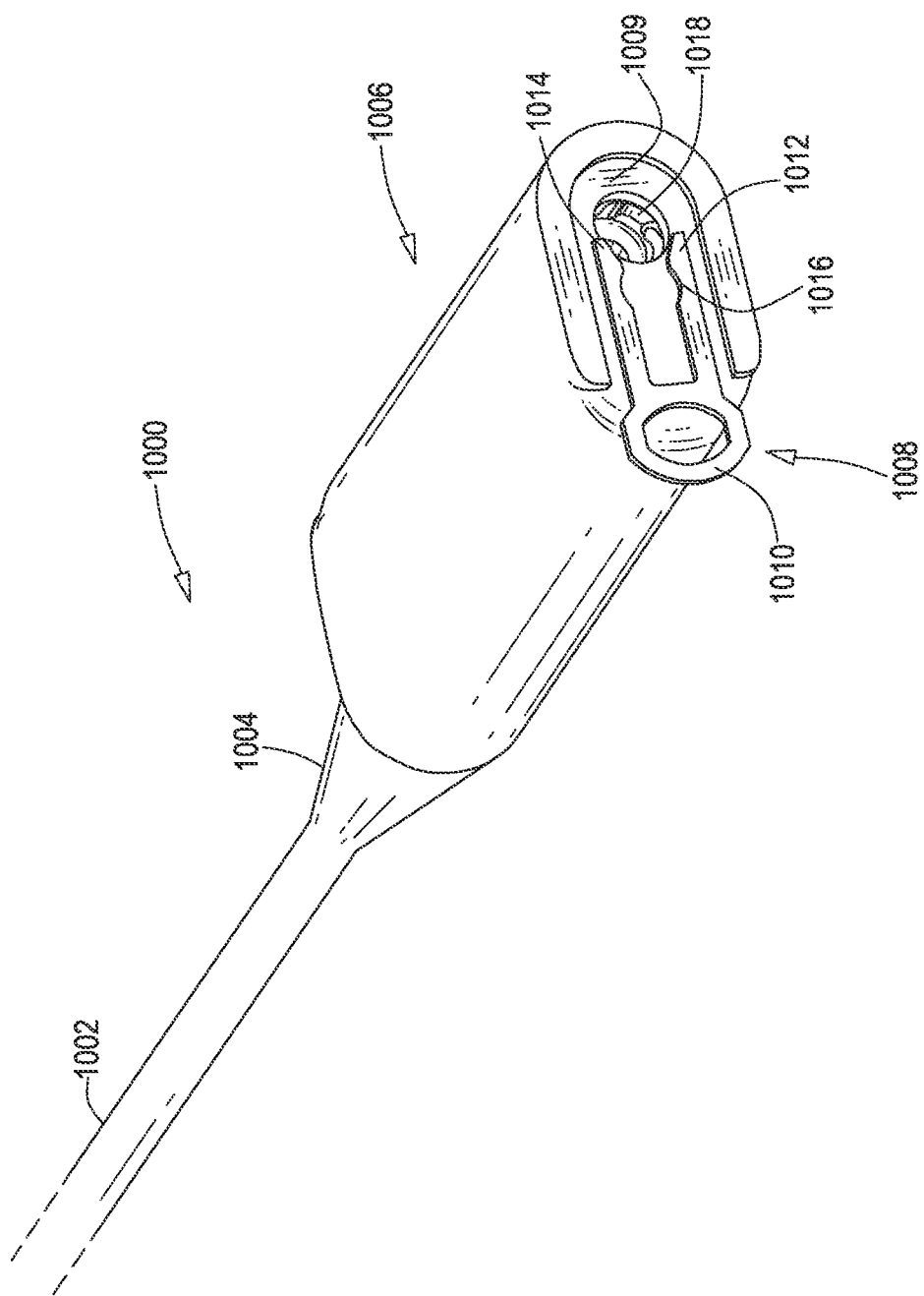
FIG. 10 shows an example of a lead extension with an extension connector assembly that receives an implantable medical lead while including a compact retention structure.

FIG. 10 shows an example of an extension 1000 having a permanently attached connector 1006 that utilizes a retention structure like that of FIGS. 8 and 9 but only for the end that receives the proximal end of the lead. The elongated portion 1002 of the extension 1000 has a permanent connection portion 1004 to the connector 1006. A movable clip 1008 having a handle 1010 is present within a groove 1009 on the opposite end of the connector 1006. The movable clip 1008 includes prongs 1012, 1014 that are springable to a more open position. This allows the prongs 1012, 1014 to be moved onto a lead body or clink as the clip 1108 is being pushed inward. The lead body or clink settles into detents 1016 in the prongs 1012, 1014 where the detents 1016 align with the bore 1018. The movable clip 1008 may be constructed of a biocompatible plastic. Where the clip 1008 can serve as a shield ground or where the clip 1008 connects only to an insulative portion of the lead, the clip 1008 may also be a biocompatible metal.

Figure 11:
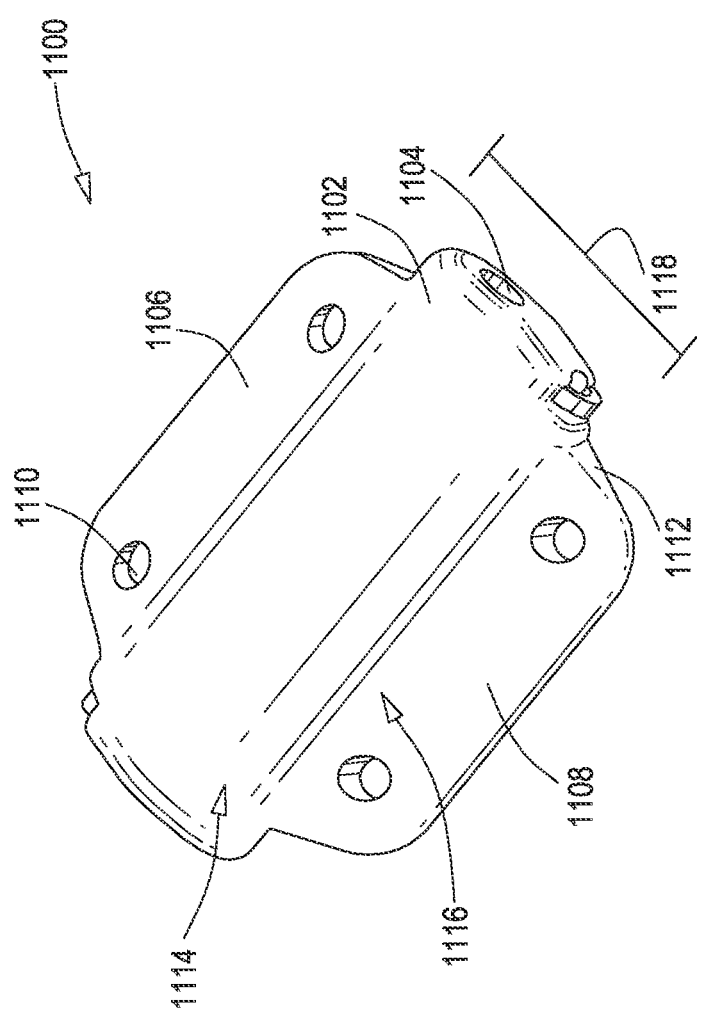
FIG. 11 shows an example of a connector assembly that receives a lead extension and an implantable medical lead while including contours that form wings.

FIG. 11 provides a view of another connector assembly 1100 that is separate from the lead extension. As can be seen, this connector assembly 1100 includes an outer layer 1102 that provides a contoured shape. The outer layer 1102 includes a flat surface 1114, a curved surface 1116 extending from the flat surface 1114, and tapered wings 1106, 1108 on each side. In this example, the taper 1112 of each wing 1106, 1108 creates a concave contour from the curved surface 1116 to the outer edge of each wing 1106, 1108. However, it will be appreciated that other contours may also be applicable such as convex, linear, and other surfaces. The taper 1112 of each wing 1106, 1108 passes through a geometric plane 1118 that passes through the bores 1104.

This contoured shape of the connector assembly 1100 reduces the likelihood of subcutaneous erosion and discomfort because of the subtle transitions the overlying tissue makes while spanning from the outer edge of wing 1106 to the outer edge of wing 1108. There are no sharp transitions, edges, and the like. Furthermore, the wings include fixation holes 1110 that allow the connector assembly 1100 to be fixed in place with screws or sutures that tighten against the underlying bone or surrounding tissue, respectively. The wings may include additional features as well, such as loops for suturing and tines for engaging the surrounding tissue to prevent relative movement. Such tines may be straight, have hooks, and so forth as discussed above in relation to the example shown in FIG. 3.

Figure 12:
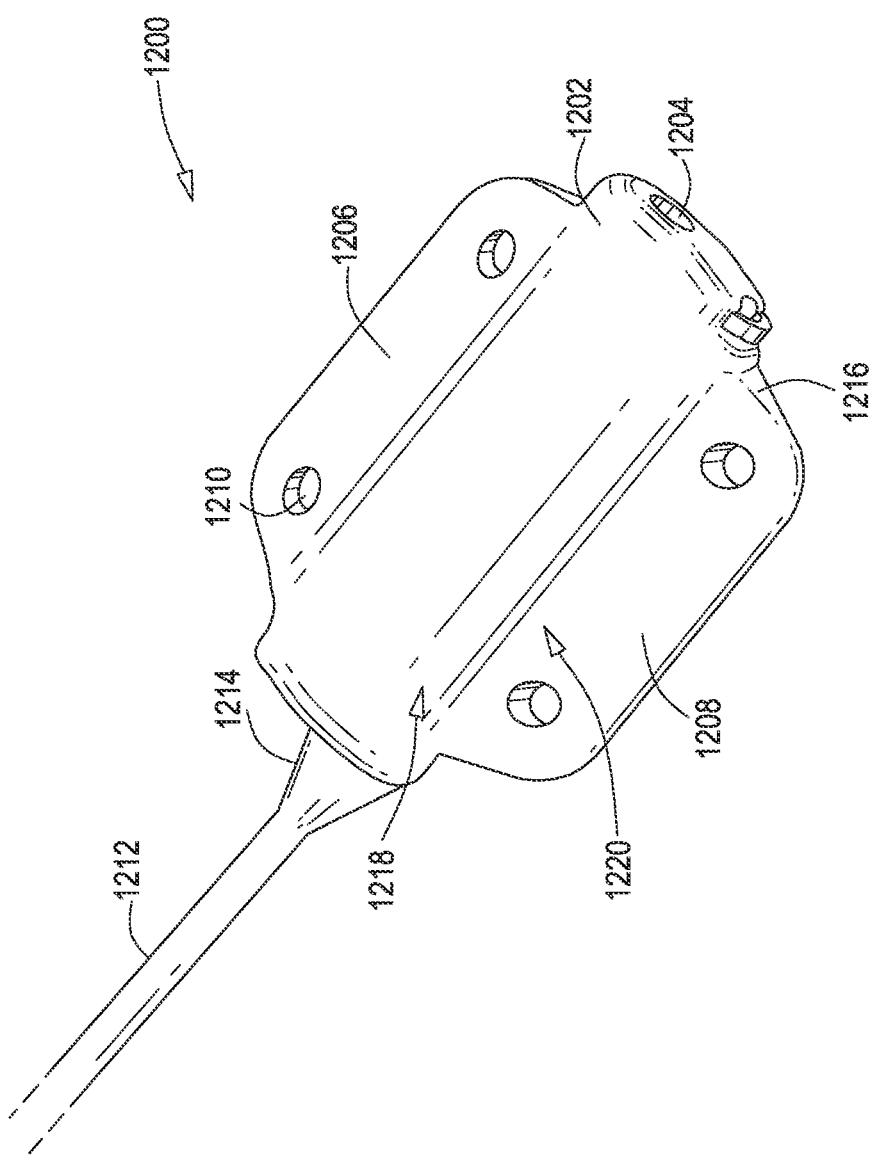
FIG. 12 shows an example of a lead extension with an extension connector assembly that receives an implantable medical lead while including contours that form wings.

FIG. 12 provides a view of another extension connector 1200 that is permanently attached to the lead extension 1212 via a portion 1214 that joins to an outer layer 1202. As can be seen, the outer layer 1202 of this connector assembly 1200 provides a contoured shape that matches that of the connector assembly FIG. 11. The outer layer 1202 includes a flat surface 1218, a curved surface 1220 extending from the flat surface 1218, and tapered wings 1206, 1208 on each side. In this example, the taper 1216 of each wing 1206, 1208 creates a concave contour from the curved surface 1220 to the outer edge of each wing 1206, 1208. The taper 1216 of each wing 1206, 1208 also passes through a geometric plane that passes through the bores 1204.

This shape of the extension connector 1200 reduces the likelihood of subcutaneous erosion because of the subtle transitions the overlying tissue makes while spanning from the outer edge of wing 1206 to the outer edge of wing 1208. There are no sharp transitions, edges, and the like. Furthermore, these wings also include fixation holes 1210 that allow the extension connector 1200 to be fixed in place with screws that tighten against the underlying bone or sutures secured to the surrounding fascia. Tines, loops, and the like may be included for this embodiment as well.

Figure 13:
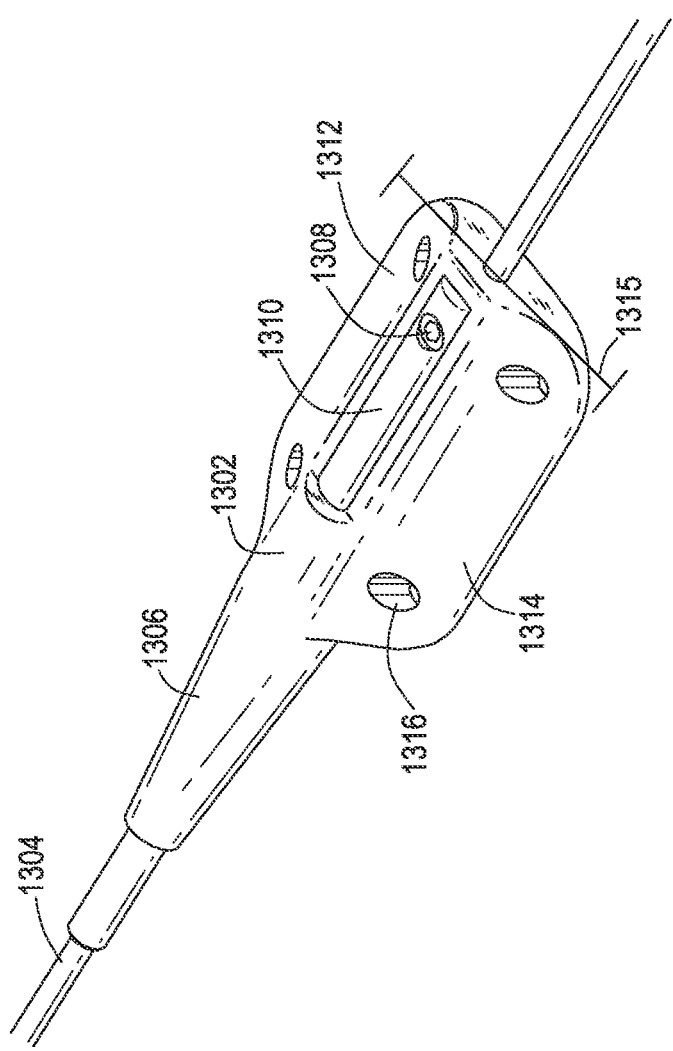
FIG. 13 shows another example of a lead extension with an extension connector assembly that receives an implantable medical lead while including contours that form wings.

FIG. 13 shows an example of another extension connector that has an outer layer 1302 which has contours and that defines a strain relief 1306 for the extension lead 1304 that is permanently attached. Here, an inner assembly 1310 is present within the outer layer 1302 which may be in the form of a boot surrounding the inner assembly except at the top where the set screw 1308 of a set screw block assembly is located. The outer layer 1302 forms contours including tapered wings 1312, 1314. In this example, the taper is a concave contour passing through a geometric plane 1315 that passes through the lead bore. Fixation holes 1316 are also present within the wings 1312, 1314 to allow for fixation to the underlying bone.

Figure 14:
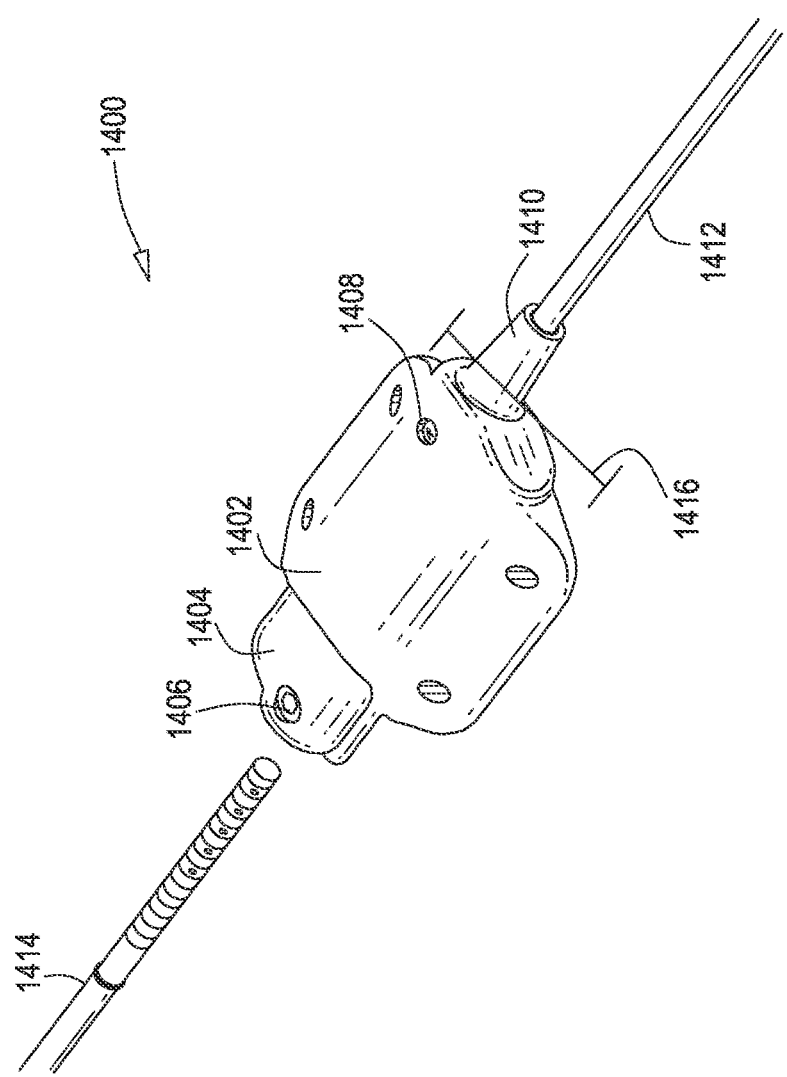
FIG. 14 shows another example of a connector assembly that receives a lead extension and an implantable medical lead while including an outer sleeve that has contours that form wings.

FIG. 14 shows another example of a connector assembly 1400 that receives both a lead 1412 and a separate lead extension 1414. An inner assembly 1404 may be at least partially surrounded by an outer layer 1402 which provides the contours including a flat surface 1402 and wings with a taper that passes through a plane 1416 that passes through the extension and lead bores. The outer layer 1402 may also provide strain relief 1410 for at least one side of the inner assembly 1404. A set screw 1406 is exposed on one side while an aperture 1408 in the outer layer 1402 may provide access to a set screw on the opposite side. The outer layer 1402 may be formed as a separate sleeve which allows the inner assembly 1404 to be inserted and removed as desired.

Figure 15:
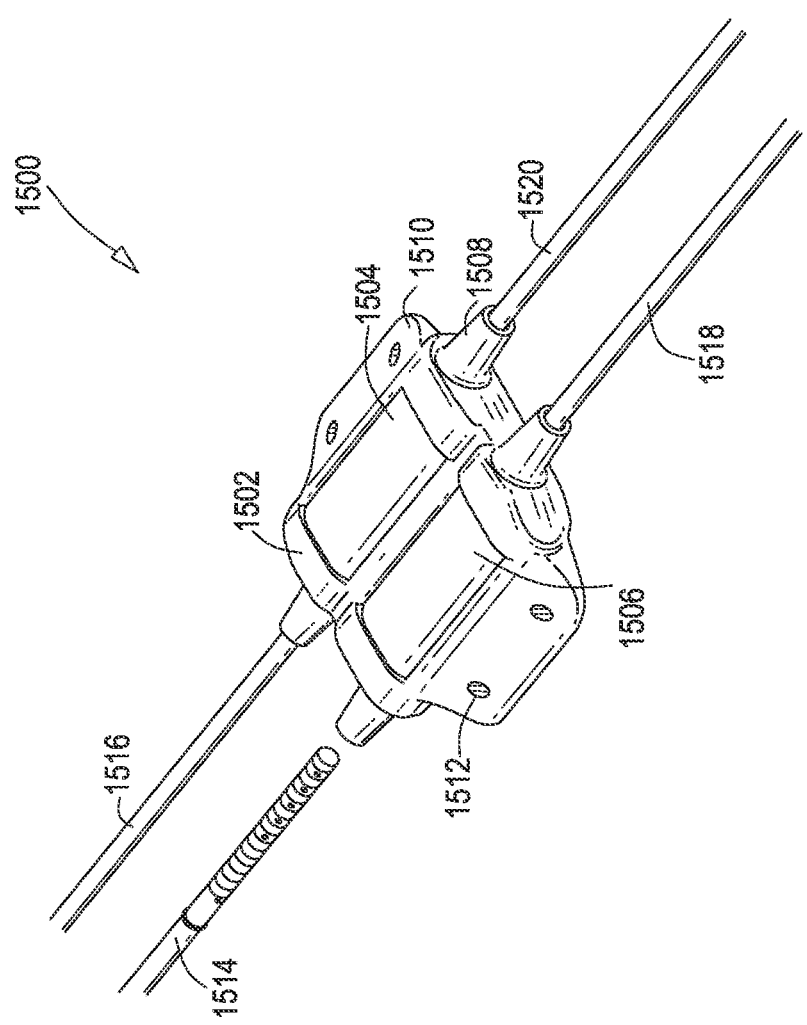
FIG. 15 shows another example of a connector assembly that receives multiple lead extensions and multiple implantable medical leads while including an outer sleeve that has contours that form wings.

FIG. 15 shows another example of a configuration 1500 of separate connector assemblies, where the configuration has an outer layer 1502 that joins to the separate inner assemblies 1504, 1506. Each inner assembly 1504, 1506 receives a lead 1518, 1520 and a separate extension 1514, 1516. The outer layer 1502 may provide strain relief 1508 for each lead and lead extension being received. Additionally, the outer layer 1502 may provide contours to lessen erosion including tapered wings 1510 which may include fixation holes 1512. The outer layer 1502 of this example is a sleeve which allows the inner assemblies 1504, 1506 to be inserted and removed as desired.

The connector assemblies discussed above receive one lead and one lead extension, or two leads and two lead extensions as in FIG. 15. However, there are many permutations that may be achieved using the configurations disclosed herein. The electrical connector bodies that provide multiple electrical connectors may be configured in various ways to connect one or more leads to one or more extensions. Several additional examples are shown in FIGS. 16A-16K.

Figure 16B:
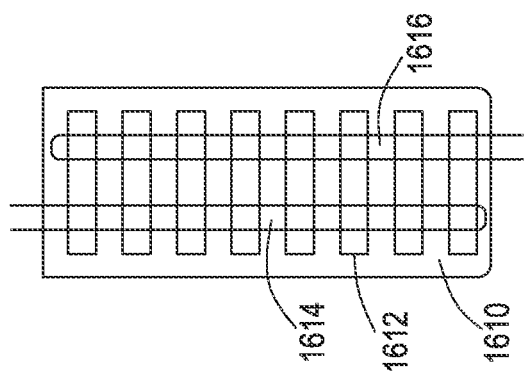
FIGS. 16A-16K show various examples of connector assembly configurations for receiving extension leads and implantable medical leads.
Figure 16A:
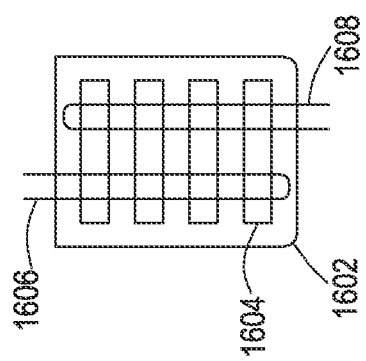

FIG. 16A shows a configuration of a connector assembly 1602 where a four electrode lead 1606 is being connected to a four conductor extension 1608. The electrical conductor bodies 1604 bridge from a connector of the extension to a connector of the lead, where the most distal electrical connector on the distal end of the extension 1608 connects to the most distal electrical connector on the proximal end of the lead 1606.

FIG. 16B shows a configuration of a connector assembly 1610 where an eight electrode lead 1614 is being connected to an eight conductor extension 1616. The electrical conductor bodies 1612 bridge from a connector of the extension to a connector of the lead, where the most distal electrical connector on the distal end of the extension 1616 connects to the most distal electrical connector on the proximal end of the lead 1614. This configuration matches the configuration of the connector assemblies of FIGS. 2-7.

Figure 16D:
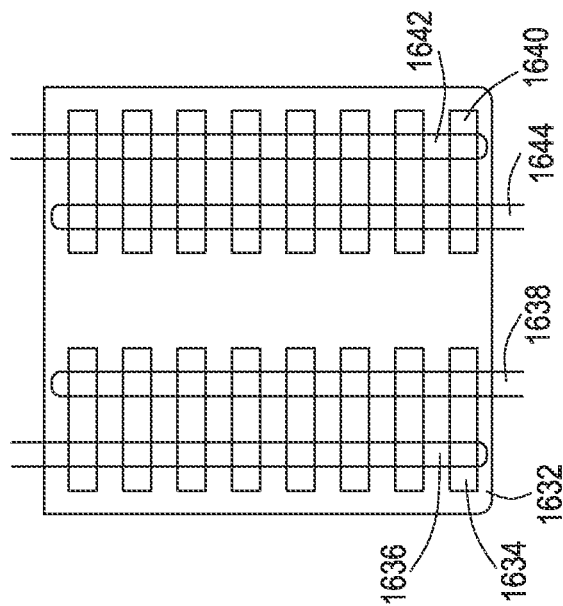
Figure 16C:
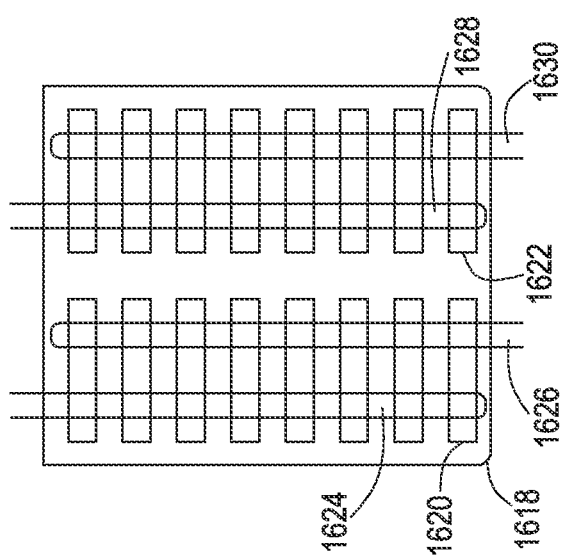

FIG. 16C shows a configuration of a connector assembly 1618 where two eight electrode leads 1624, 1628 are being connected to two eight conductor extensions 1626, 1630. The electrical conductor bodies 1620, 1622 bridge from a connector of each extension 1626, 1630 to a connector of each corresponding lead 1624, 1628, where the most distal electrical connector on the distal end of the extensions 1626, 1630 connects to the most distal electrical connector on the proximal end of the leads 1624, 1628. Also in this configuration, both extensions are positioned on the same side of their respective leads. This configuration is similar to the configuration of the connector assembly of FIG. 15 except that this configuration is a single connector assembly body while FIG. 15 shows two separate connector assembly bodies 1504, 1506 joined by the outer sleeve.

FIG. 16D shows a configuration of a connector assembly 1632 which is much like the connector assembly 1618 of FIG. 16C. Two eight electrode leads 1636, 1642 are being connected to two eight conductor extensions 1638, 1644. The electrical conductor bodies 1634, 1640 bridge from a connector of each extension 1638, 1644 to a connector of each corresponding lead 1636, 1642, where the most distal electrical connector on the distal end of the extensions 1638, 1644 connects to the most distal electrical connector on the proximal end of the leads 1636, 1642. However, in this configuration the extensions are positioned on opposite sides of their respective leads from one another.

Figure 16F:
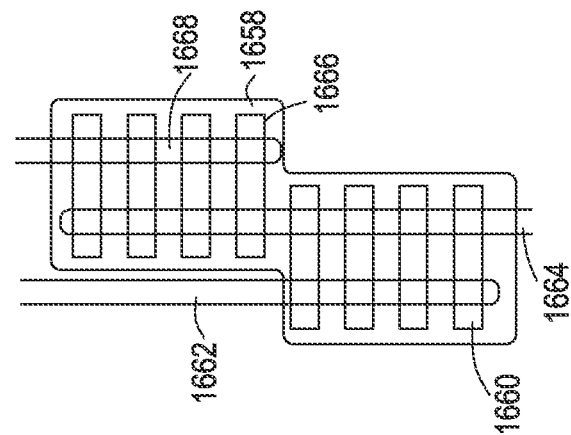
Figure 16E:
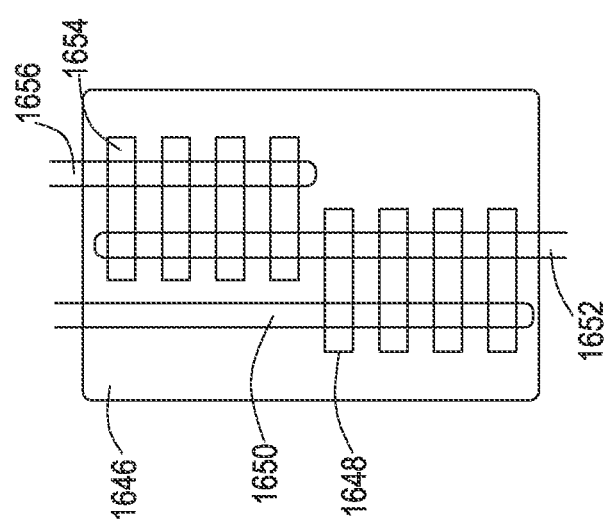

FIG. 16E shows a configuration of a connector assembly 1646 where two four electrode leads 1650, 1656 are being connected to one eight conductor extension 1652. Four conductors of the extension 1652 correspond to one lead 1650, and the other four conductors of the extension 1652 correspond to the other lead 1656. A first set of electrical conductor bodies 1648 interconnect the connectors of the lead 1650 to the corresponding connectors of the extension 1652 while a second set 1654 of electrical conductor bodies that are offset from the first set 1648 interconnect the connectors of the lead 1656 to the corresponding connectors of the extension 1652. In this configuration, the lead 1650 is inserted into the connector assembly roughly twice as far as the lead 1656.

FIG. 16F shows a configuration of a connector assembly 1658 which is much like the configuration of the connector assembly 1646 in FIG. 16E. Two four electrode leads 1662, 1668 are being connected to one eight conductor extension 1664. Four conductors of the extension 1664 correspond to one lead 1662, and the other four conductors of the extension 1664 correspond to the other lead 1668. A first set of electrical conductor bodies 1660 interconnect the connectors of the lead 1662 to the corresponding connectors of the extension 1664 while a second set of electrical conductor bodies 1666 that are offset from the first set 1660 interconnect the connectors of the lead 1668 to the corresponding connectors of the extension 1664. In this configuration, the outer body of the connector assembly 1658 is shaped such that the lead 1662 is not inserted into the connector assembly 1658 any farther than the lead 1656.

Figure 16H:
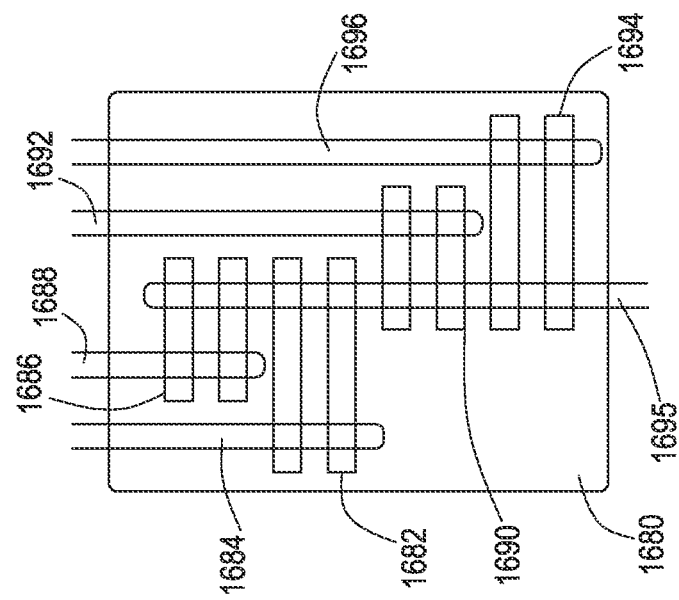
Figure 16G:
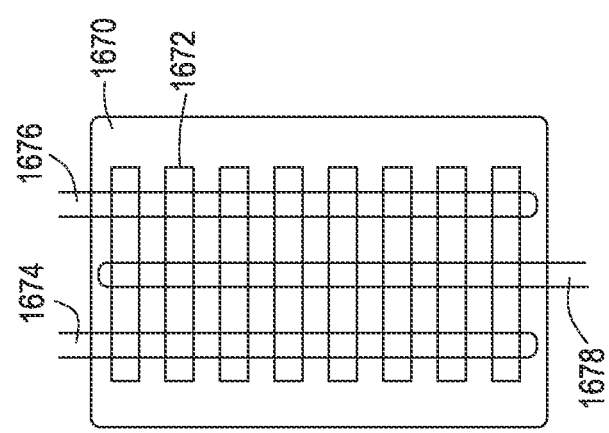

FIG. 16G shows a configuration where two eight electrode leads 1674, 1676 are being connected to one eight conductor extension 1678 so as to gang fire the electrodes of the two leads 1674, 1676. The electrical conductor bodies 1672 bridge from a connector of the extension to a connector of both of the leads 1674, 1676, where the most distal electrical connector on the distal end of the extension 1678 connects to the most distal electrical connectors on the proximal end of both of the leads 1674, 1676. Thus, in this configuration, the electrical conductor bodies 1672 have three electrical connections instead of two.

FIG. 16H shows a configuration of a connector assembly 1680 where four two electrode leads 1684, 1688, 1692, and 1696 are being connected to one eight conductor extension 1695. The electrical conductor bodies of a first set 1682 bridge from a connector of the extension 1695 to a corresponding connector of the lead 1684. These electrical conductor bodies are of a length that spans two lead bore widths from the bore of the extension 1695. The electrical conductor bodies of a second set 1686 bridge from a connector of the extension 1695 to a corresponding connector of the lead 1688. These electrical conductor bodies are of a length that spans only one lead bore width from the bore of the extension 1695. The electrical conductor bodies of a third set 1690 bridge from a connector of the extension 1695 to a corresponding connector of the lead 1692. These electrical conductor bodies are of a length that spans only one lead bore width from the bore of the extension 1695. The electrical conductor bodies of a fourth set 1694 bridge from a connector of the extension 1695 to a corresponding connector of the lead 1696. These electrical conductor bodies are also of a length that spans two lead bore widths from the bore of the extension 1695. As can be seen, in this configuration lead 1684 is inserted twice the distance of lead 1688, lead 1692 is inserted three times as far, and lead 1696 is inserted four times as far.

Figure 16J:
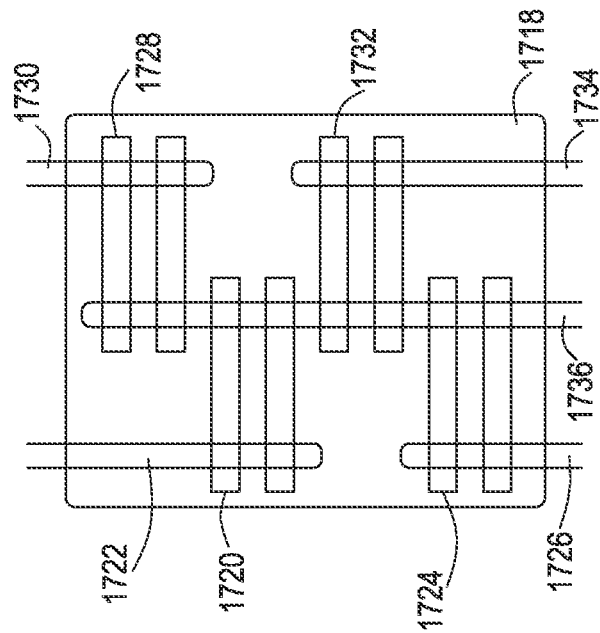
Figure 16I:
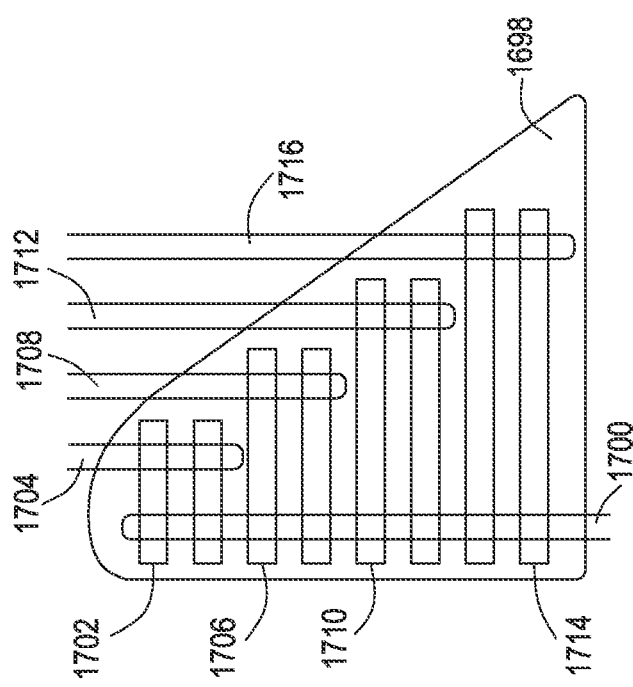

FIG. 16I shows a configuration of a connector assembly 1698 that is similar to the configuration of FIG. 16H in that four two electrode leads 1704, 1708, 1712, and 1716 are being connected to one eight conductor extension 1700. The electrical conductor bodies of a first set 1702 bridge from a connector of the extension 1700 to a corresponding connector of the lead 1704. The electrical conductor bodies of a second set 1706 bridge from a connector of the extension 1700 to a corresponding connector of the lead 1708. These electrical conductor bodies are of a length that spans two lead bore widths from the bore of the extension 1700. The electrical conductor bodies of a third set 1710 bridge from a connector of the extension 1700 to a corresponding connector of the lead 1712. These electrical conductor bodies are of a length that spans three lead bore widths from the bore of the extension 1700. The electrical conductor bodies of a fourth set 1714 bridge from a connector of the extension 1700 to a corresponding connector of the lead 1716. These electrical conductor bodies are also of a length that spans four lead bore widths from the bore of the extension 1700. As can be seen, in this configuration the leads are all inserted the same distance into the connector assembly 1698.

FIG. 16J shows a configuration of a connector assembly 1718 that is similar to the configurations of FIGS. 16H and 16I in that four two electrode leads 1722, 1726, 1730, and 1734 are being connected to one eight conductor extension 1736. The electrical conductor bodies of a first set 1720 bridge from a connector of the extension 1736 to a corresponding connector of the lead 1722. The electrical conductor bodies of a second set 1724 bridge from a connector of the extension 1736 to a corresponding connector of the lead 1726. The electrical conductor bodies of a third set 1728 bridge from a connector of the extension 1736 to a corresponding connector of the lead 1730. The electrical conductor bodies of a fourth set 1732 bridge from a connector of the extension 1736 to a corresponding connector of the lead 1734. As can be seen, in this configuration the leads 1722 and 1734 are inserted into the connector assembly 1718 twice the distance as leads 1726 and 1730. Furthermore, leads 1726 and 1734 are inserted on the same side as the extension 1736. It will be appreciated that the lead and the extension can be inserted on the same side of the connector assembly for any of the embodiments discussed herein.

Figure 16K:
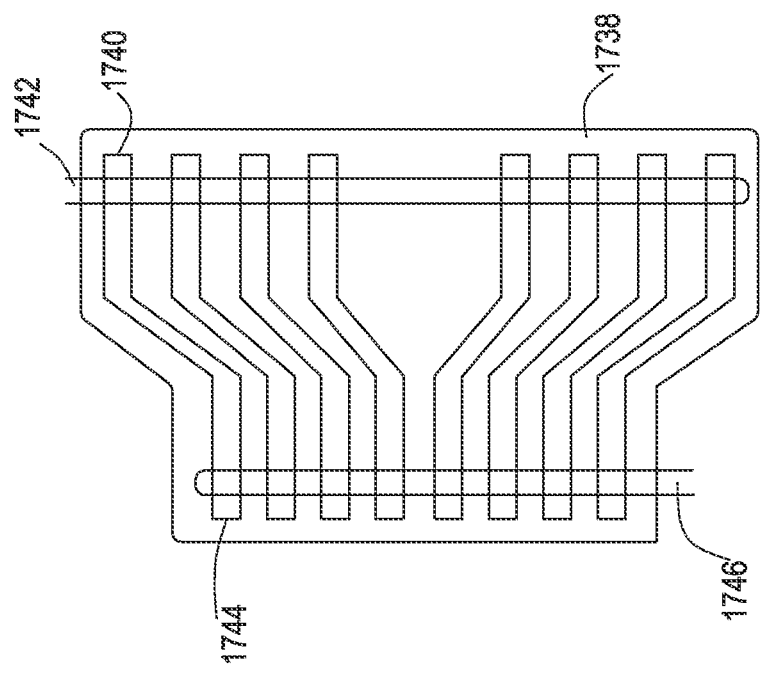

FIG. 16K shows a configuration of a connector assembly 1738 where one eight electrode lead 1742 is being connected to one eight conductor extension 1746. In this example, however, the pitch of the connectors on the lead 1740 is greater than the pitch of the connectors on the extension 1746. To account for this, the electrical conductor bodies are not straight but instead have an angular section that forms an angle relative to the lateral dimension of the connector assembly 1738. Each electrical conductor body forms an angular section with a slightly different angle than the adjacent electrical conductor body. Thus, the pitch at the ends 1744 of the electrical conductor bodies in the bore for the extension 1746 is different than the pitch of the ends 1740 of the same electrical conductor bodies in the bore for the lead 1742. While the lead is shown with two sets of four connections, the spacing between the fourth and the fifth connections could be made to maintain the pitch for all eight connections.

The pitch within a given connector assembly may be chosen so as to be universal relative to a collection of leads having different pitches. For example, a connector assembly having a pitch of 0.085" for eight connectors can accommodate a lead having a proximal end with eight or fewer connectors at 0.085", or a lead having up to four proximal connectors with a 0.170" pitch. Thus, the connector assembly can be applicable to this universe of lead options. This universal aspect also applies to receiving a collection of lead extensions that may have different pitches and number of connectors.

Figure 17:
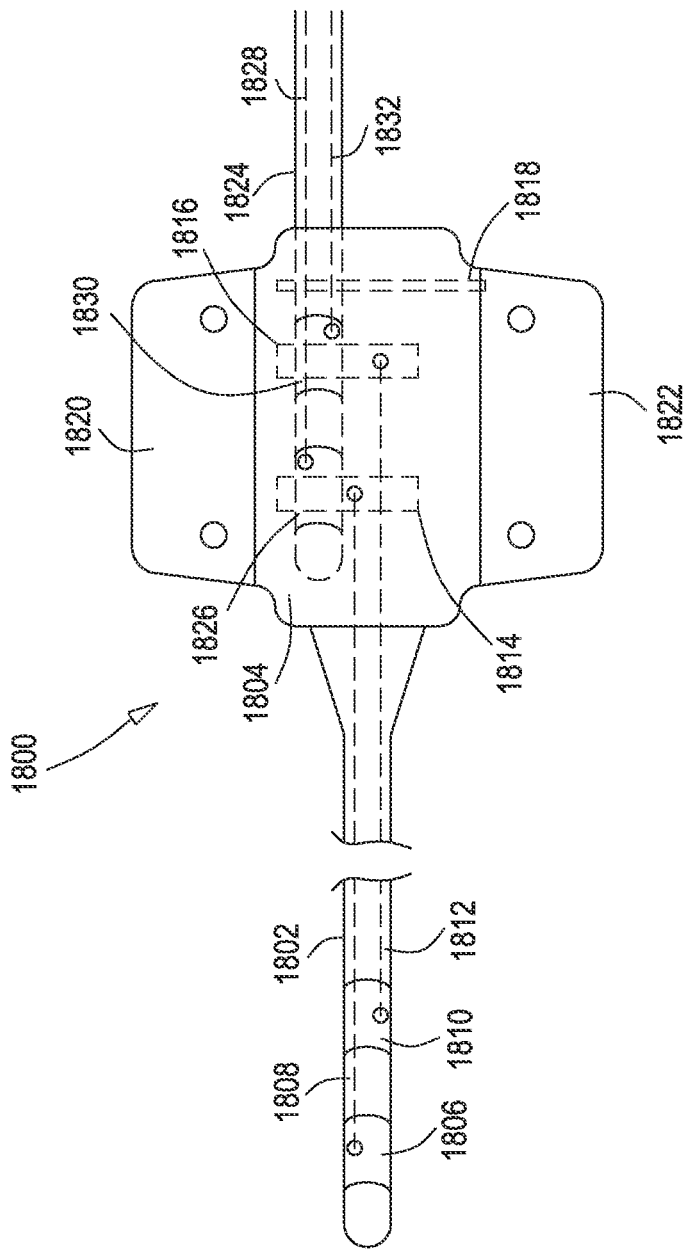
FIG. 17 shows an example of a lead extension with an extension connector assembly that includes a compact retention structure and that receives an implantable medical lead while including contours that form wings.

FIG. 17 shows a lead extension 1800 and demonstrates the electrical pathways that are present, as well as the wings and the lead retention structure that are present. For clarity of illustration, only two electrical pathways are shown but it will be appreciated that any number of electrical pathways may exist in a lead extension to lead connection. The lead extension 1800 includes the lead extension elongated portion formed by an elongated insulated body 1802 and the lead extension connector portion 1804 that is permanently attached to the elongated body 1802. While the portion 1804 is shown as being centered to the connector portion 1804, it may alternatively be offset. The elongated body 1802 includes electrical connectors 1806, 1810 with electrically conductive filars 1808, 1812 connected to the respective electrical connectors 1806, 1810. The filars 1808, 1812 extend into the connector portion 1804 where each establishes an electrical connection to a respective electrical connector body 1814, 1816.

The connector portion 1804 includes a lead bore that receives a lead 1824. The lead 1824 includes two proximal electrodes 1826, 1830 and respective electrical conductors 1828, and 1832 that extend to the distal end electrodes of the lead 1824. The electrical conductor bodies 1814 and 1816 serve to bridge each electrical path from the conductors 1808, 1812 to the connectors 1826, 1830, respectively. These connector bodies 1814, 1816 may be of various forms including the two connection single piece connectors discussed above in relation to FIG. 6.

The connector portion 1804 includes contours that define tapered wings 1820, 1822 like those discussed above in relation to FIGS. 12 and 13. These contoured wings help prevent erosion by eliminating abrupt features and by also providing a stable anchor to the underlying bone to prevent movement of the connector portion 1804.

The connector portion 1804 also includes a compact retention structure, rather than a set screw block assembly. In this example, the connector portion 1804 includes a movable clip 1818 that can be moved into and out of engagement with the lead 1824. This movable clip 1818 may be within a groove and may be shaped and function like the movable clip of FIG. 10 discussed above.

Figure 18A:
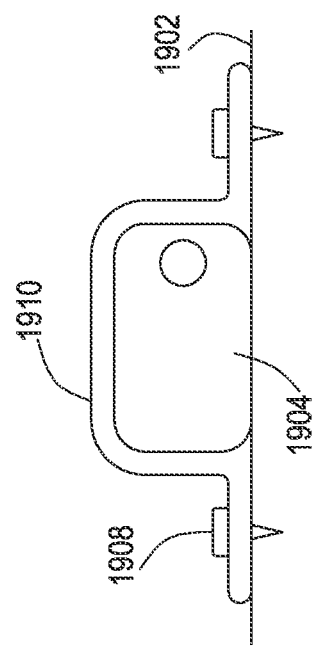

FIGS. 18A-18D show various configurations for anchoring a separate connector assembly or a connector portion of a lead extension. By anchoring the connector assembly, stresses imposed on the connector by the extension are not passed along to the implanted lead which improves reliability. As shown in FIG. 18A, the connector assembly or connector portion 1904 is positioned within a pit that a surgeon has made within a bone 1902. An anchoring strap 1906 is placed over the pit and is secured to the bone with screws 1908 to hold the connector 1904 within the pit. The anchoring strap 1906 may be constructed of soft or rigid materials such as a plastic or a metal.

Figure 18B:
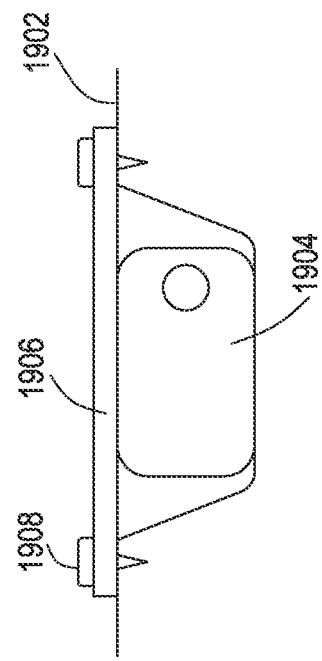

In FIG. 18B, the connector 1904 sits on a bone 1902. An anchor strap 1910 is placed over the connector 1904 and the anchor strap 1910 is shaped so as to also engage the bone 1902. Screws 1908 secure the strap 1910 to the bone 1902 so that the strap 1910 holds the connector 1904 in a fixed position. The anchoring strap 1910 may be constructed of a rigid material such as a plastic or a metal.

In FIG. 18C, a connector holder 1912 has arms 1914 that fit around the connector 1904 which sits atop the holder 1912. The holder 1912 sits atop the bone. In this example, the holder 1912 is fixed relative to the bone 1902 with a screw 1908 located beneath the connector 1904. The holder 1912 may be constructed of a rigid material such as a plastic or a metal. In this example, the single bone screw 1908 allows the connector holder 1912, and the connector 1904 within it, to be swiveled which may be a benefit to surgeons during the implantation procedure.

In FIG. 18D, a connector assembly or connector portion 1916 of a lead extension has anchor portions 1918 built in. The anchor portions 1918 are fixed to the bone 1902 with screws 1908. In some embodiments, these anchor portions 1918 may be tapered wings as discussed above for purposes of reducing erosion.

Figure 19A:
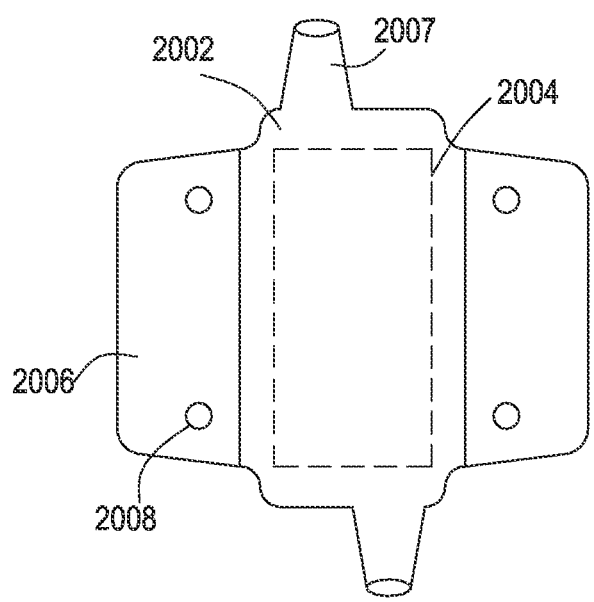
FIGS. 19A-19C show various examples of contoured anchors for connector assemblies.
Figure 19B:
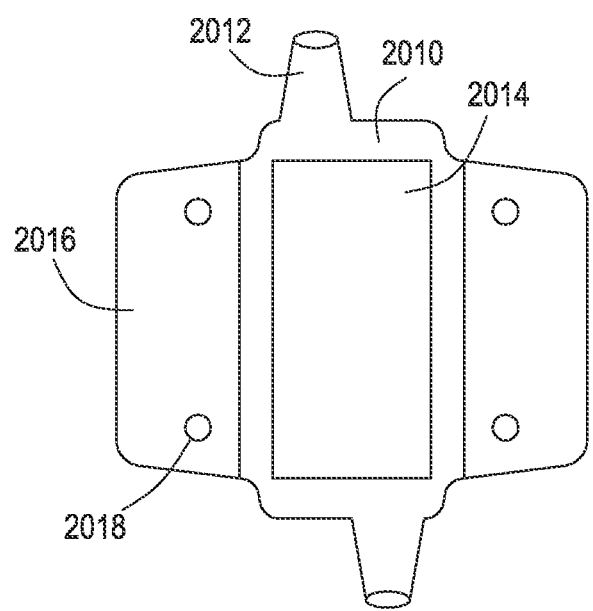
Figure 19C:
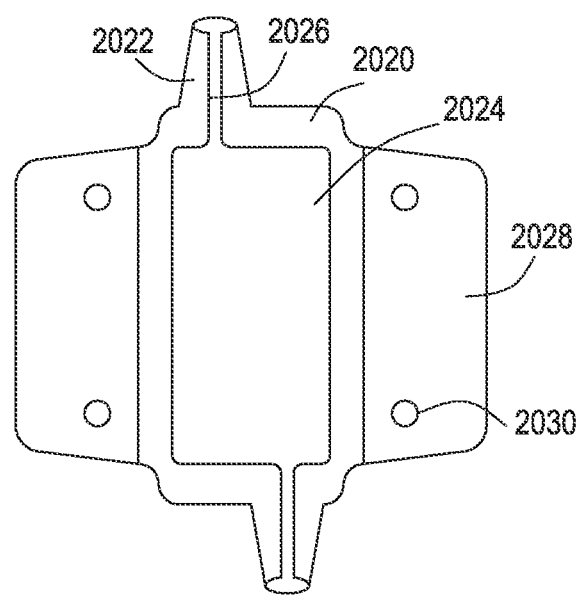

FIGS. 19A-19C show various configurations for including wings for a separate connector assembly or a connector portion of a lead extension. In FIG. 19A, an outer layer 2002 that has been overcoated atop the connector 2004 provides wings 2006 with fixation holes 2008. A strain relief 2007 is also shown. This overcoated outer layer 2002 as well as the overcoated layers of embodiments previously discussed herein may be made of liquid silicone rubber, polyurethane, and the like and may be produced by various techniques such as over-molding, heath shrinking, or swelled silicone. Furthermore, the wings of any of FIGS. 19A-19C may be removable by being perforated so as to be torn away, or may be trimmed with scissors.

In FIG. 19B, a sleeve 2010 has an opening 2014 that allows the separate connector to be positioned within the sleeve 2010 prior to the lead and lead extension being connected to the connector. This sleeve 2010 provides wings 2016 with fixation holes 2018. A strain relief 2012 is also shown. This sleeve 2010 may be made of liquid silicone rubber and the like.

In FIG. 19C, a sleeve 2020 has an opening 2024 that allows the separate connector or the extension connector of a lead extension to be inserted. The separate connector may be inserted into the opening 2024 either before the lead and lead extension have been connected or after they have been connected, which provides the surgeon with added flexibility. Similarly, an extension connector can be inserted into the opening 2024 either before the lead has been connected or after it has been connected, which again provides the surgeon with added flexibility. This is made possible by the sleeve 2020 also having slots 2026 that extend from the opening 2024 to the lead bore openings of the strain relief 2022 on both sides. These slots 2026 allow for the passage of the lead and the lead extension cable when inserting the connector through the opening 2024. This sleeve 2020 may be made of liquid silicone rubber and the like.

Figure 20:
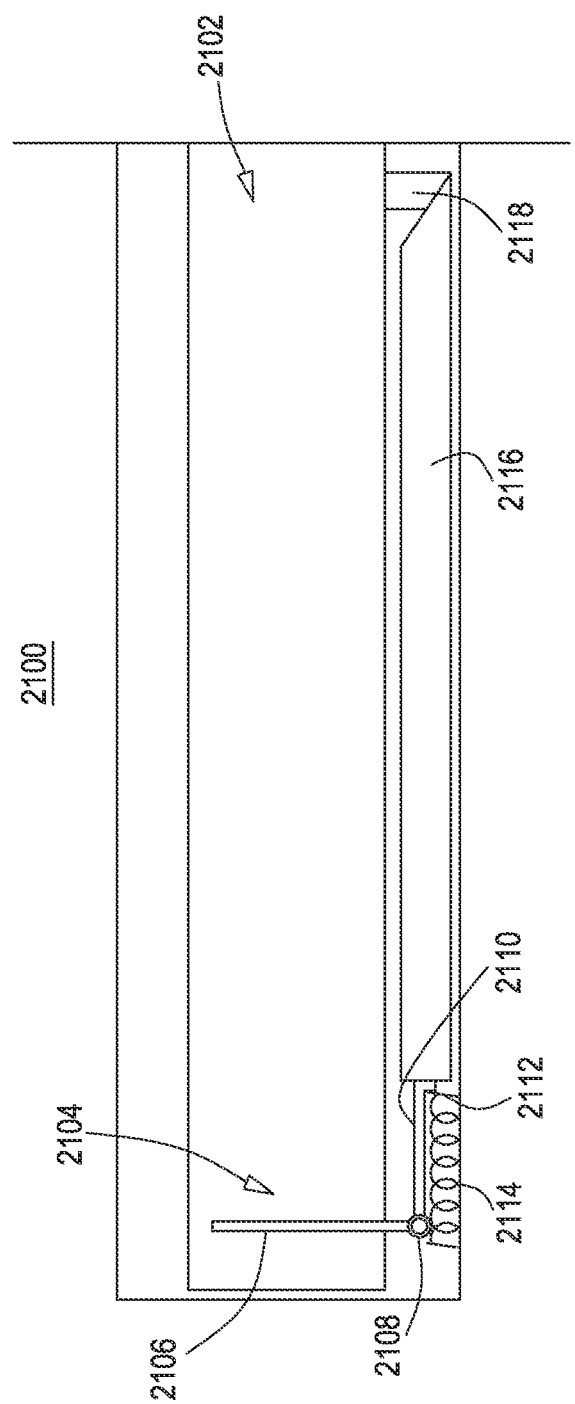
FIG. 20 shows a spring loaded retention structure in an untripped state.

FIG. 20 shows an example of a connector 2100 such as a separate connector assembly or a connector permanently attached on an extension. A retention structure 2104 is a spring loaded mechanism that includes a contact arm 2106 that pivots about a hinge point 2108. A retainer arm 2110 includes a retainer 2112 that retains a spring 2114 in a compressed state. A push arm 2116 extends from the retainer 2112 to a lock arm 2118. The push arm 2116 and the lock arm 2118 of this example have angled surfaces in contact to transfer longitudinal movement of the push arm 2116 into lateral movement of the lock arm 2118. As shown in FIG. 20, the lock arm 2118 is not within the bore 2102 such that the lead or extension can slide into or out of the bore 2102 without restriction by the lock arm 2118.

Figure 21:
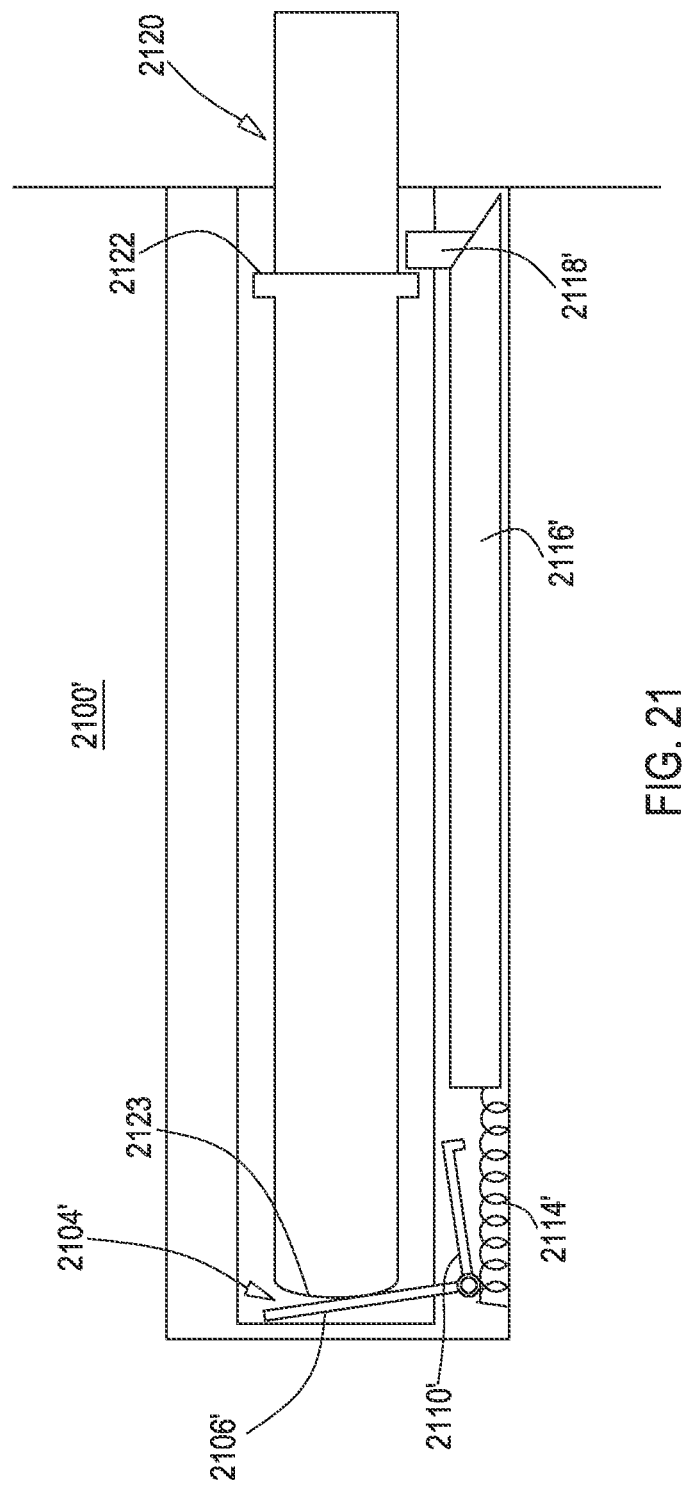
FIG. 21 shows the spring loaded retention structure in a tripped state.

As shown in FIG. 21, upon the lead or extension 2120 being inserted, the tip 2123 contacts and moves the contact arm 2106' to the position shown. Movement of the contact arm 2106' thereby moves the retainer arm 2110 to the position shown, thereby releasing the retainer 2112 from the spring 2114. The spring 2114 forces the push arm 2116 longitudinally toward the lock arm 2118 which thereby forces the lock arm 2118 laterally into the bore 2120. The lock arm 2118 engages a flange 2122 of the lead or extension 2120 to lock the lead or extension 2120 in place within the bore 2102.

Figure 22:
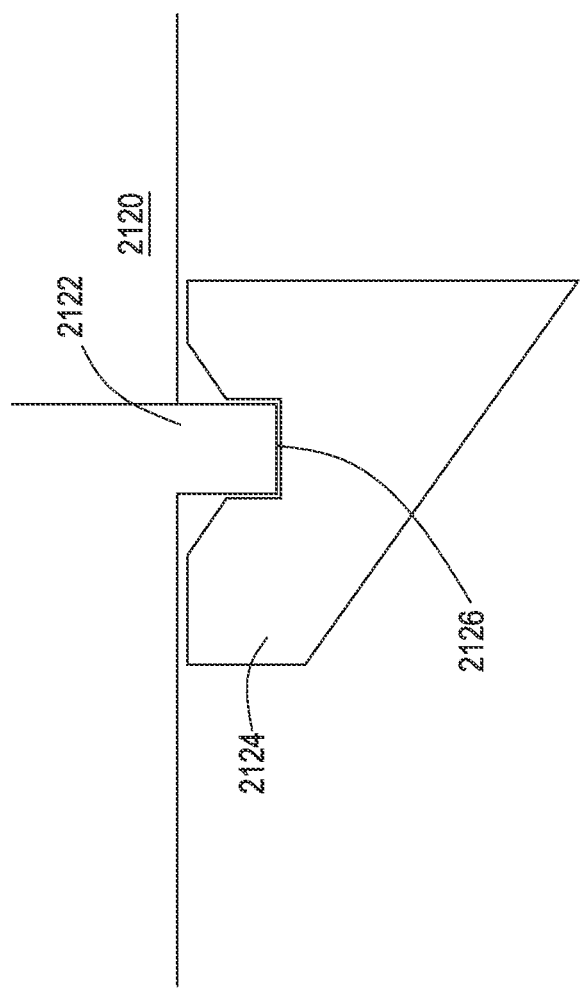
FIG. 22 shows an alternative catch of the spring loaded mechanism.

FIG. 22 shows an alternative where the lock arm 2124 that includes a detent 2126. The flange 2122 becomes seated within the detent 21226 upon the lock arm 2124 being forced into the bore 2102 to thereby lock the lead or extension 2120 in place within the bore 2102.

Figure 23:
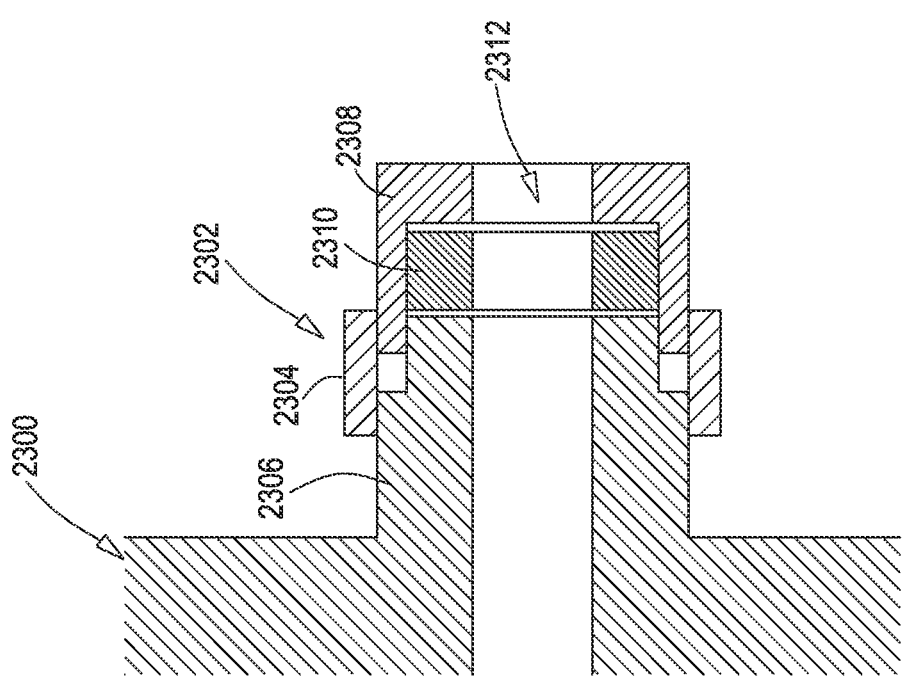
FIG. 23 shows a twist lock retention structure in an unengaged state.

FIG. 23 shows an example of a connector 2300 such as a separate connector assembly or a connector permanently attached on an extension. A retention structure 2302 is a twist lock mechanism that includes a twistable portion 2304 that is rotationally coupled to a protrusion 2306 of the connector 2300 and to a coupling 2308 while being aligned with the bore 2312. Rotation of the portion 2304 causes the coupling 2308 move toward or away from the protrusion 2306. A deformable ring 2310 is retained within a gap between the protrusion 2306 and the coupling 2308. As shown in FIG. 23, when the ring 2310 is not being squeezed, the ring 2310 does not deform into the bore 2312, and the lead or extension can be inserted or removed without restriction by the ring 2310.

Figure 24:
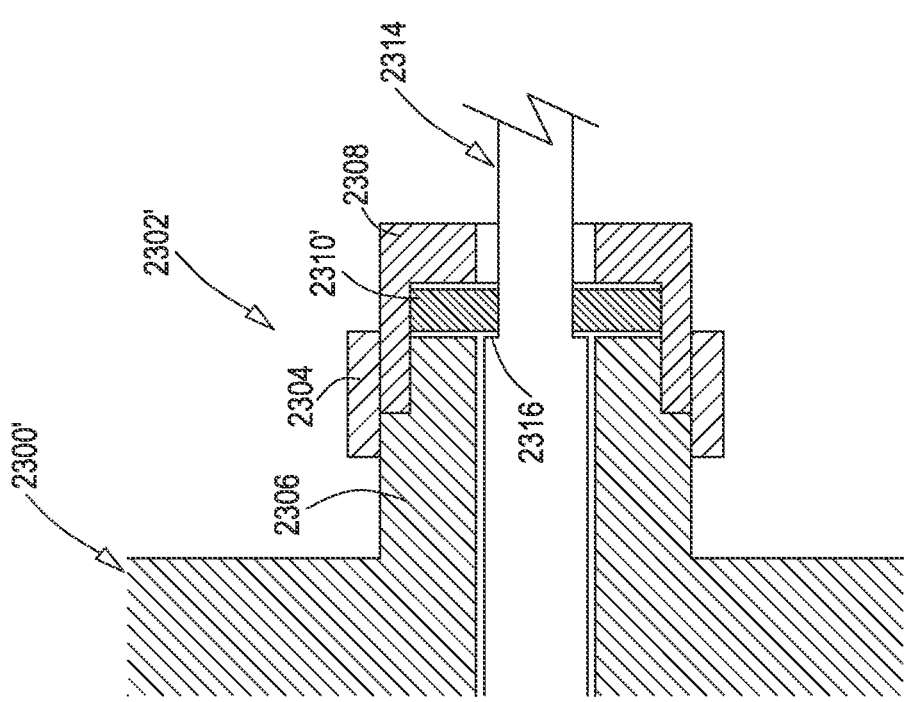
FIG. 24 shows the twist lock retention structure in an engaged state.

As shown in FIG. 24, upon rotating portion 2304, the coupling 2308 is pulled toward the protrusion 2306 to squeeze the ring 2310. The ring 2310 then deforms into the bore 2312 to thereby engage a flange 2316 of the lead or extension 2314 present within the bore 2312, to thereby lock the lead or extension 2314 in place within the bore 2312.

While embodiments have been particularly shown and described, it will be understood by those skilled in the art that various other changes in the form and details may be made therein without departing from the spirit and scope of the invention.

What is claimed is:

1. An implantable lead extension for receiving an implantable medical lead, comprising:
    an elongated insulative body having a proximal end and a distal end;
    a plurality of electrical connectors on the proximal end;
    a plurality of filars present within the elongated body and being electrically connected to corresponding electrical connectors;
    an extension connector assembly permanently attached to the distal end of the elongated body, the extension connector assembly comprising:
        a body housing a first bore; and
        a spring loaded retention structure within the first bore, the spring loaded retention structure comprising a contact arm, a spring, and a lock arm, wherein the contact arm extends laterally across the first bore and is connected to a hinge point of the extension connector assembly such that movement of the contact arm releases the spring from a compressed state, the lock arm being mechanically coupled to the spring such that when the spring is released from the compressed state, the lock arm moves laterally into the first bore.

2. An implantable lead extension for receiving an implantable medical lead, comprising:
    an elongated insulative body having a proximal end and a distal end;
    a plurality of electrical connectors on the proximal end;
    a plurality of filars present within the elongated body and being electrically connected to corresponding electrical connectors;
    an extension connector assembly permanently attached to the distal end of the elongated body, the extension connector assembly comprising:
        a body housing a first bore and a groove perpendicular to the first bore, the groove housing a movable clip, the movable clip having a springable end such that movement of the clip moves the springable end into and out of alignment with the first bore; and
        a plurality of electrical connectors within the first bore, the plurality of filars being electrically connected to corresponding electrical connectors within the first bore, wherein the body houses a second bore with an external opening, the body including a plurality of insulative spacers having apertures that are aligned adjacently to define the first bore and the second bore; each electrical connector of the plurality of electrical connectors of the first bore being separated from an adjacent electrical connector of the plurality electrical connectors of the first bore by an insulative spacer of the plurality of insulative spacers;
    a second plurality of electrical connectors further defining the second bore, the electrical connectors of the first plurality being paired and electrically coupled to corresponding electrical connectors of the second bore, wherein the electrical connectors of the first bore are at a pitch different than the electrical connectors of the second bore.

* * * * *